(12) United States Patent
Reuveni et al.

(10) Patent No.: US 9,073,880 B2
(45) Date of Patent: Jul. 7, 2015

(54) 2-(2-PHENYLETHENYL) 1,3-BENZODIAZEPINE DERIVATIVES USEFUL FOR THE TREATMENT OF CANCER

(75) Inventors: Hadas Reuveni, Har-Adar (IL); Alexander Levitzki, Jerusalem (IL)

(73) Assignee: Yissum Research Development Company of the Hebrew University of Jeruselem Ltd., Jerusalem (IL)

( * ) Notice: Subject to any disclaimer, the term of this patent is extended or adjusted under 35 U.S.C. 154(b) by 104 days.

(21) Appl. No.: 13/976,876

(22) PCT Filed: Dec. 27, 2011

(86) PCT No.: PCT/IL2011/050078
§ 371 (c)(1),
(2), (4) Date: Jun. 27, 2013

(87) PCT Pub. No.: WO2012/090204
PCT Pub. Date: Jul. 5, 2012

(65) Prior Publication Data
US 2013/0274251 A1 Oct. 17, 2013

Related U.S. Application Data

(60) Provisional application No. 61/427,220, filed on Dec. 27, 2010, provisional application No. 61/504,722, filed on Jul. 6, 2011.

(51) Int. Cl.
*C07D 279/08* (2006.01)
*A61K 31/5415* (2006.01)
*A61K 45/06* (2006.01)

(52) U.S. Cl.
CPC .......... *C07D 279/08* (2013.01); *A61K 31/5415* (2013.01); *A61K 45/06* (2013.01)

(58) Field of Classification Search
CPC ... C07D 279/08; A61K 31/5415; A61K 45/06
See application file for complete search history.

(56) References Cited

U.S. PATENT DOCUMENTS 5,217,999 A 6/1993 Levitzki
5,773,476 A 6/1998 Chen

FOREIGN PATENT DOCUMENTS

WO WO99/24442 5/1999
WO WO2008/068751 A1 6/2008
WO WO2009/147682 A1 12/2009

OTHER PUBLICATIONS

Aaronson (1991) Growth factors and cancer. Science 254(5035): 1146-1153.
Backstrom et al., (1989) Synthesis of some novel potent and selective catechol O-methyltransferase inhibitors. J Med Chem 32(4): 841-846.
Baserga (2009) The insulin receptor substrate-1: a biomarker for cancer? Exp Cell Res 315(5): 727-732.
Berge et al., (1977) Pharmaceutical salts. J Pharm Sci 66(1): 1-19.
Cardone et al., (1998) Regulation of cell death protease caspase-9 by phosphorylation. Science 282(5392): 1318-1321.
Gazit et al., (1989) Tyrphostins I: synthesis and biological activity of protein tyrosine kinase inhibitors. J Med Chem 32 (10): 2344-2352.
Goodson (1984) Dental applications. In: Medical Applications of Controlled Release, vol. II, pp. 115-138, Langer and Wise, Eds. Boca Raton: CRC Press, Inc.
Langer (1990) New methods of drug delivery. Science 249(4976): 1527-1533.
Levitzki et al., (1990) Tyrphostins—potential antiproliferative agents and novel molecular tools. Biochem Pharmacol 40 (5): 913-918.
Levitzki (1992) Tyrphostins: tyrosine kinase blockers as novel antiproliferative agents and dissectors of signal transduction. FASEB J 6(14): 3275-3282.
Levitzki and Gazit (1995) Tyrosine kinase inhibition: an approach to drug development. Science 267(5205): 1782-1788.
Li et al., (2009) Inhibition of the insulin-like growth factor-1 receptor (IGF1R) tyrosine kinase as a novel cancer therapy approach. J Med Chem 52(16): 4981-5004.
Posner et al., (1994) Kinetics of inhibition by typhostins of the tyosine kinase activity of the epideral gowth facor receptor and analysis by a new computer program. Mol Pharmacol 45(4): 673-683
Ravikumar et al., (2007) Insulin receptor substrate-1 is an important mediator of ovarian cancer cell growth suppression by all-trans retinoic acid. Cancer Res 67(19): 9266-9275.
Ryan and Goss (2008) The emerging role of the insulin-like growth factor pathway as a therapeutic target in cancer. Oncologist 13(1): 16-24.

(Continued)

*Primary Examiner* — Sarah Pihonak
(74) *Attorney, Agent, or Firm* — Winston & Strawn LLP

(57) ABSTRACT

The present invention provides compounds of formula (1) acting as protein kinase (PK) and receptor kinase (RK) signaling modulators. The invention further provides methods of their preparation, pharmaceutical compositions including such compounds, and methods of using these compounds and compositions, especially as anti-cancer agents for preventions and treatments of PK- and RK-related disorders, in particular cancer. (I) wherein A is H or CN; Z is S, SO or $SO_2$; $X^1, X^2, X^3, X^4, X^5, Y^1$ and $Y^2$ are each independently selected from H, halogen, alkyl, haloalkyl and $OR^1$; and $Y^3$ and $Y^4$ are each $OR^1$, wherein each $R^1$ is independently H, $C_1$-$C_4$ alkyl, acyl, —$(CH_2CH_2O)_n$ wherein n is an integer of 1 to 20, or a functional group that gives rise to hydroxyl upon hydrolysis.

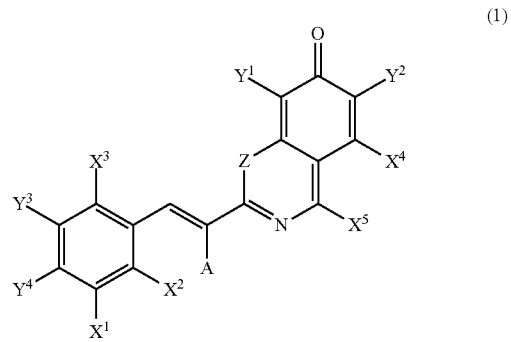

(1)

18 Claims, 9 Drawing Sheets

(56) References Cited

OTHER PUBLICATIONS

Saudek et al., (1989) A preliminary trial of the programmable implantable medication system for insulin delivery. N Engl J Med 321(9): 574-579.
Schlessinger (1988) Signal transduction by allosteric receptor oligomerization. Trends Biochem Sci 13(11): 443-447.
Schlessinger and Ullrich (1992) Growth factor signaling by receptor tyrosine kinases. Neuron 9(3): 383-391.
Ullrich and Schlessinger (1990) Signal transduction by receptors with tyrosine kinase activity. Cell 61(2): 203-212.
Yaish et al., (1988) Blocking of EGF-dependent cell proliferation by EGF receptor kinase inhibitors. Science 242(4880): 933-935.
Yoneda et al., (1991) The antipolfertive effects of tyrosine kinase inhibitors tyrphostins on a human squamous cell carcinoma in vitro and in nude mice. Cancer Res 51(16): 4430-4435.

2-(2-PHENYLETHENYL) 1,3-BENZODIAZEPINE DERIVATIVES USEFUL FOR THE TREATMENT OF CANCER

CROSS REFERENCE TO RELATED APPLICATIONS

This application claims the benefit of U.S. Provisional Patent Applications Nos. 61/427,220 filed Dec. 27, 2010 and 61/504,722 filed Jul. 6, 2011.

FIELD OF THE INVENTION

The present invention relates to compounds which modulate protein kinase signaling and their use in treatment of protein kinase related disorders. Methods for their preparation and methods of use thereof are provided.

BACKGROUND OF THE INVENTION

Protein kinases (PKs) are a family of enzymes, which are involved in a variety of cellular processes, including signal transduction and growth regulation. Protein kinases (PKs) remove the γ-phosphate from ATP and covalently attach it to one of three amino acids that have a free hydroxyl group on substrate proteins. Most kinases act on both serine and threonine, others act on tyrosine, and a number (dual specificity kinases) act on all three. These phosphorylation processes by PKs are key events in cellular signaling.

Receptor tyrosine kinases (RTKs) constitute one class of protein tyrosine kinases (PTKs). These kinases belong to a family of transmembrane proteins and have been implicated in cellular signaling pathways. The predominant biological activity of some receptor kinases is the stimulation of cell growth and proliferation, while other receptor tyrosine kinases are involved in inhibiting growth and promoting differentiation. In some instances, a single tyrosine kinase can inhibit, or stimulate, cell proliferation depending on the cellular environment in which it is expressed (Schlessinger and Ullrich, *Neuron* (1992), 9(3): 383-391). RTKs include receptors for platelet-derived growth factor (PDGF), fibroblast growth factor (FGF), hepatocyte growth factor (HGF), insulin, insulin-like growth factor 1 (IGF-1), nerve growth factor (NGF), vascular endothelial growth factor (VEGF), macrophage colony stimulating factor (M-CSF) and others.

Receptor tyrosine kinases are mainly composed of an extracellular glycosylated ligand binding domain, a transmembrane domain and a cytoplasmic catalytic domain that can phosphorylate tyrosine residues. Binding of a ligand to membrane-bound receptors induces the formation of receptor dimers and allosteric changes thus activating the intercellular kinase domains which further results self-phosphorylation (autophosphorylation and/or transphosphorylation) of the receptor on tyrosine residues. Receptor phosphorylation stimulates physical association of the activated receptor with target molecules. Some of the target molecules are, in turn, phosphorylated, a process which transmits the signal to the cytoplasm. The secondary signal transducer molecules generated by activated receptors, result in a signal cascade that regulates cell functions such as cell division or differentiation. Intracellular signal transduction is reviewed in Aaronson, *Science* (1991), 254: 1146-1153; Schlessinger, *J. Trends Biochem. Sci.* (1988), 13: 443-447; and Ullrich and Schlessinger, *Cell* (1990), 61: 203-212.

Various cell proliferative disorders have been associated with defects in pathways mediated by PTKs. Enhanced activities of PTKs resulting from overexpression of the normal kinase, upregulation of ligands of receptor tyrosine kinases or activating mutations, are a hallmark of many diseases which involve cellular proliferation, including cancer. Examples of specific receptor tyrosine kinases associated with cell proliferative disorders include platelet derived growth factor receptor (PDGFR), insulin-like growth factor 1 receptor (IGF-1R), epidermal growth factor receptor (EDFR), and the related HER2.

The involvement of PTKs in various diseases renders them as targets for antiproliferative drugs. Numerous PTK blockers have been described in the literature including proposed mechanisms of action (Levitzki et al., *Science* (1995), 267: 1782-88; and Posner et al., *Mol. Pharmacol.* (1994), 45: 673-683). A family of PTK inhibitors, named tyrphostins, designed to mimic the tyrosine substrate was disclosed in Levitzki et al., *Science* (1995), 267: 1782-88; Levitzki et al., *Biochem. Pharm.* (1990), 40: 913-920; Levitzki et al., *FASEB J.* (1992), 6: 3275-3282; U.S. Pat. Nos. 5,217,999 and 5,773,476. The pharmacophores of these tyrphostins, and in particular tyrphostins of the benzylidene malonitril type, are the hydrophilic catechol ring and the more lipophilic substituted cyano-vinyl radical. Kinetic studies have shown that some tyrphostin compounds are pure competitive inhibitors vis-à-vis tyrosine substrates whereas for the ATP binding site they act as non-competitive inhibitors (Yaish et al., *Science* (1988), 242: 933-935; and Gazit et al., *J. Med. Chem.* (1989), 32: 2344-2352). Nonetheless, many tyrphostins have shown competitive inhibition against both the substrate and ATP binding site (Posner et al., *Mol. Pharmacol.* (1994), 45: 673-683).

In a related group of tyrphostins, the hydrophilic catechol ring was exchanged by lipophilic dichloro- or dimethoxyphenyl groups, to yield EGFR kinase inhibitors, effective in the low micromolar range (Yoneda et al., *Cancer Res.* (1991), 51: 4430-4435). These tyrphostins were further administered to tumor-bearing nude mice together with anti-EGFR monoclonal antibodies at a suboptimal dose to afford markedly enhanced inhibition of tumor growth.

WO 99/24442 discloses compounds for inhibiting intracellular signal transduction mediated by one or more molecular interactions involving a phosphotyrosine-containing protein.

WO 2008/068751 to some of the inventors of the present invention, discloses novel tyrphostins compounds having increased inhibitory properties of insulin-like growth factor 1 receptor (IGF-1R), platelet derived growth factor receptor (PDGFR), epidermal growth factor receptor (EGFR), and IGF-1R-related insulin receptor (IR) activation and signaling.

WO 2009/147682 to some of the inventors of the present invention, discloses new tyrphostin derivatives acting as protein kinase (PK) and receptor kinase (RK) signaling modulators.

SUMMARY OF THE INVENTION

The present invention relates to compounds which modulate protein kinase (PK) activity, activation and signaling in cells. These compounds show inhibition of human cancer cell proliferation thus being potent for the treatment of diseases which are associated with altered or abnormal activity or signaling of protein kinases, e.g. cancer, psoriasis, or metabolic or fibrotic disorders. In some embodiments, the novel compounds of the invention show increased inhibitory properties of, but not limited to, insulin-like growth factor 1 receptor (IGF-1R), platelet derived growth factor receptor (PDGFR), epidermal growth factor receptor (EGFR), and IGF1R-related insulin receptor (IR), or proteins affected by or mediated by these PTKs or that are part of the PTK-mediated signal transduction pathway. For example, as demonstrated herein, the compounds of the present invention are potent inhibitors of insulin-like growth factor 1 receptor (IGF-1R) and/or insulin receptor substrate 1 (IRS1) and/or insulin receptor substrate 2 (IRS2) signaling. As such, these compounds are useful in inhibiting, treating or preventing an IGF-1R and/or IRS1 and/or IRS2 signaling related disorder, for example cancer. In some embodiments, the compounds of the invention trigger any one or more of the following, in any order: (i) serine phosphorylation of the IGF-1R direct substrates IRS1 and/or IRS2; (ii) dissociation of IRS1 and/or IRS2 from the cell membrane; and/or (iii) degradation of IRS1 and/or IRS2, thus providing long-lasting effects which enhance the inhibitory activity of these novel compounds.

According to one aspect, the present invention provides compounds represented by the structure of formula 1:

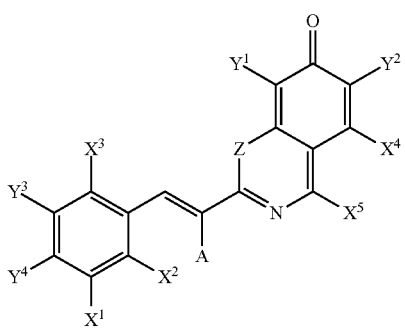

1 wherein
A is H or CN;
Z is S, SO or $SO_2$;
$X^1$, $X^2$, $X^3$, $X^4$, $X^5$, $Y^1$ and $Y^2$ are each independently selected from H, halogen, alkyl, haloalkyl and $OR^1$; and $Y^3$ and $Y^4$ are each $OR^1$, wherein each $R^1$ is independently H, $C_1$-$C_4$ alkyl, —$(CH_2CH_2O)_n$ wherein n is an integer of 1 to 20, acyl or a functional group that gives rise to hydroxyl upon hydrolysis, including salts, hydrates, solvates, polymorphs, optical isomers, geometrical isomers, enantiomers, diastereomers, and mixtures thereof.

In one embodiment, the present invention provides a compound represented by the structure of formula 1, wherein A is H. In another embodiment, the present invention provides a compound represented by the structure of formula 1, wherein A is CN. In some embodiments, the present invention provides a compound represented by the structure of formula 1, wherein Z is S. In other embodiments, the present invention provides a compound represented by the structure of formula 1, wherein Z is $SO_2$. In certain embodiments, the present invention provides a compound represented by the structure of formula 1, wherein at least one of $X^1$, $X^2$, $X^3$, $X^4$, $Y^1$ and $Y^2$ is a halogen. In other embodiments, the present invention provides a compound represented by the structure of formula 1, wherein at least one of $X^1$, $X^2$, $X^3$, $X^4$, $Y^1$ and $Y^2$ is Br. In some embodiments, the present invention provides a compound represented by the structure of formula 1, wherein at least one of $X^1$, $X^2$, $X^3$, $X^4$, $Y^1$ and $Y^2$ is I. In certain embodiments, the present invention provides a compound represented by the structure of formula 1, wherein $X^1$, $X^2$, $X^3$, and $X^4$ are each selected from H or a halogen, wherein the halogen is preferably Br or I. In certain embodiments, the present invention provides a compound represented by the structure of formula 1, wherein $X^2$ is H. In certain embodiments, the present invention provides a compound represented by the structure of formula 1, wherein $X^5$ is H. In certain embodiments, the present invention provides a compound represented by the structure of formula 1, wherein $X^5$ is alkyl, preferably methyl. In some embodiments, the present invention provides a compound represented by the structure of formula 1, wherein $Y^3$ and $Y^4$ are each OH. In other embodiments, the present invention provides a compound represented by the structure of formula 1, wherein $Y^1$ and $Y^2$ are each OH. In particular embodiments, the present invention provides a compound represented by the structure of formula 1, wherein A is H, Z is S, $Y^3$ and $Y^4$ are each OH, and $X^1$ is a halogen selected from Br and I. Each possibility represents a separate embodiment of the present invention.

In other embodiments, the present invention provides a compound represented by the structure of formula 1, wherein A is CN, Z is S, $Y^3$ and $Y^4$ are each OH, and $X^1$ is a halogen selected from Br and I. Each possibility represents a separate embodiment of the present invention. In yet other embodiments, the present invention provides a compound represented by the structure of formula 1, wherein A is H, Z is S, $Y^3$ and $Y^4$ are each OH, and $X^3$ is a halogen selected from Br and I. Each possibility represents a separate embodiment of the present invention. In further embodiments, the present invention provides a compound represented by the structure of formula 1, wherein A is H, Z is S, $Y^3$ and $Y^4$ are each OH, and $X^2$ is a halogen selected from Br and I. Each possibility represents a separate embodiment of the present invention. In additional embodiments, the present invention provides a compound represented by the structure of formula 1, wherein A is H, Z is S, $Y^3$ and $Y^4$ are each OH, and $X^1$ and $X^4$ are each a halogen selected from Br and I. In yet other embodiments, the present invention provides a compound represented by the structure of formula 1, wherein A is H, Z is $SO_2$, $Y^3$ and $Y^4$ are each OH, and $X^1$ is a halogen selected from Br and I. In yet other embodiments, the present invention provides a compound represented by the structure of formula 1, wherein A is H, Z is $SO_2$, $Y^3$ and $Y^4$ are each OH, and at least one of $X^1$, $X^2$, $X^3$, $X^4$, $Y^1$ and $Y^2$ is a halogen. Each possibility represents a separate embodiment of the present invention.

Representative and non-limiting examples of such structures are compounds selected from the group consisting of:

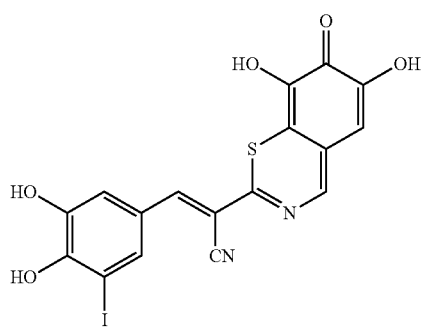

2

3
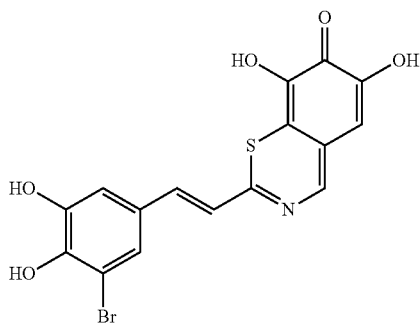

4
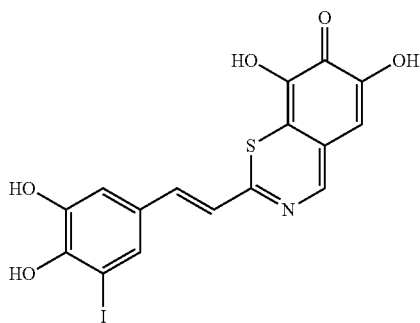

5
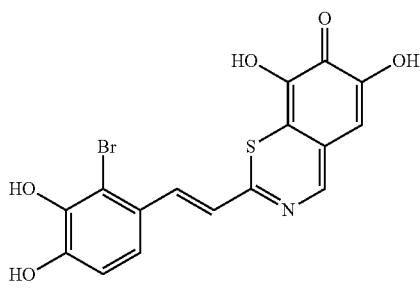

6
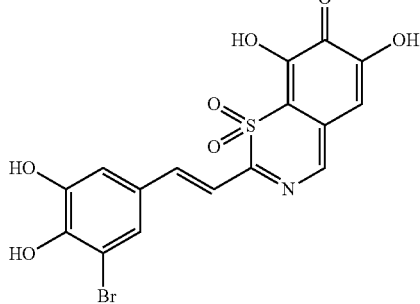

7
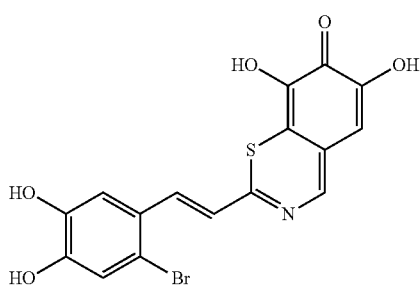

8
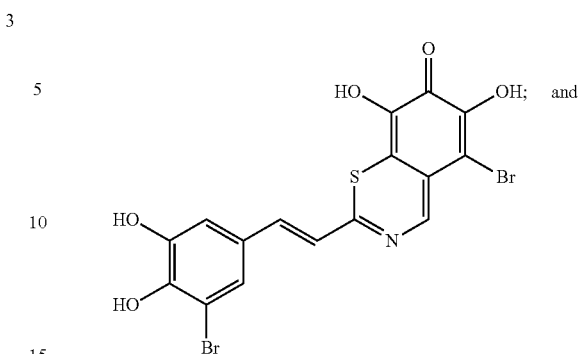

9
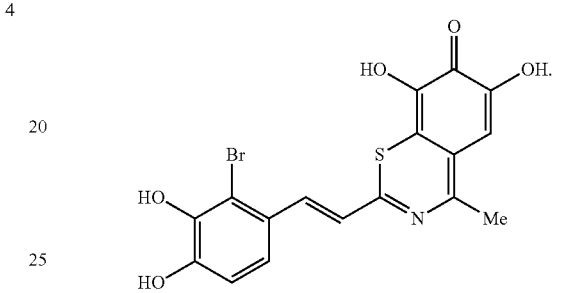

The above compounds may be isolated from any medium containing them. Accordingly, in some embodiments, the present invention provides isolated compounds represented by the general structure of formula 1, or any compounds encompassed by this generic structure including, but not limited to, compounds 2, 3, 4, 5, 6, 7, 8 or 9. Each of these compounds represents a separate embodiment of the present invention.

The present invention further provides a pharmaceutical composition comprising a therapeutically effective amount of at least one compound represented by the structure of formula 1.

1
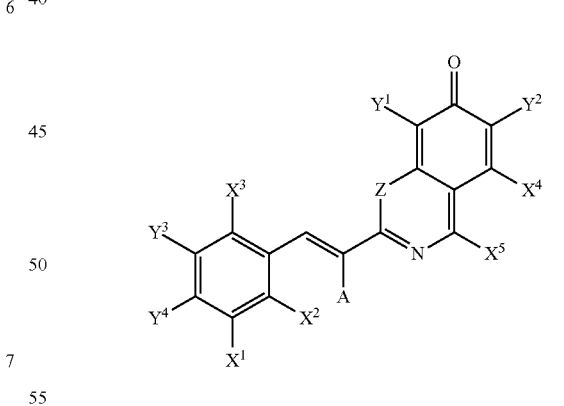

wherein
A is H or CN;
Z is S, SO or $SO_2$;
$X^1$, $X^2$, $X^3$, $X^4$, $X^5$, $Y^1$ and $Y^2$ are each independently selected from H, halogen, alkyl, haloalkyl and $OR^1$; and
$Y^3$ and $Y^4$ are each $OR^1$, wherein each $R^1$ is independently H, $C_1$-$C_4$ alkyl, —$(CH_2CH_2O)_n$ wherein n is an integer of 1 to 20, acyl or a functional group that gives rise to hydroxyl upon hydrolysis, including salts, hydrates, solvates, polymorphs, optical isomers, geometrical isomers, enantiomers, diastereomers, and mixtures thereof; and a pharmaceutically acceptable carrier or excipient.

In some embodiments, the present invention provides a pharmaceutical composition comprising a therapeutically effective amount of at least one compound represented by the structure of formula 1, for example at least one of compounds 2-9 and a pharmaceutically acceptable carrier or excipient.

In another aspect, the present invention provides a method of inhibiting signal transduction mediated by a protein kinase (PK) in a cell, comprising contacting the cell with a pharmaceutical composition comprising a therapeutically effective amount of at least one compound represented by the structure of formula 1 or at least one of compounds 2-9.

In an additional aspect, the present invention provides a method of inhibiting cell proliferation comprising contacting the cell with a pharmaceutical composition comprising a therapeutically effective amount of at least one compound represented by the structure of formula 1 or at least one of compounds 2-9.

In another embodiment, the present invention provides a method of inhibiting protein kinase (PK) activity, activation or signaling in a subject comprising the step of administering to the subject a pharmaceutical composition comprising a therapeutically effective amount of at least one compound represented by the structure of formula 1 or at least one of compounds 2-9. In some embodiments, the method comprises administering to the subject a therapeutically effective amount of at least one compound represented by the structure of formula 1, or at least one of compounds 2-9 and a pharmaceutically acceptable carrier or excipient.

In various embodiments, the present invention further provides a method of inhibiting, treating or preventing a protein kinase (PK) related disorder in a subject comprising the step of administering to the subject a pharmaceutical composition comprising a therapeutically effective amount of at least one compound represented by the structure of formula 1 or at least one of compounds 2-9. In other embodiments, the method comprises administering to the subject a pharmaceutical composition comprising a therapeutically effective amount of at least one compound represented by the structure of formula 1, or at least one of compounds 2-9 and a pharmaceutically acceptable carrier or excipient. In one embodiment, the PK related disorder is a disorder related to receptor protein tyrosine kinase (RPTK). In some embodiments, the receptor protein tyrosine kinase, according to the principles of the present invention, is selected from a platelet-derived growth factor receptor (PDGFR), a fibroblast growth factor receptor (FGFR), a hepatocyte growth factor receptor (HGFR), an insulin receptor, an insulin-like growth factor-1 receptor (IGF-1R), an epidermal growth factor receptor (EGFR), a nerve growth factor receptor (NGFR), a vascular endothelial growth factor receptor (VEGFR), and a macrophage colony stimulating factor (M-CSFR). Each possibility represents a separate embodiment of the present invention.

Without being bound to any particular theory or mechanism of action, it is contemplated that the compounds of the present invention are inhibitors of PK signaling, such as IGF-1R. It has now been surprisingly been found that these compounds, in addition to being inhibitors of IGF-1R, also lead to the dissociation of the IGF-1R substrates IRS1/2 from the cell membrane, inhibitory serine phosphorylation and/or irreversible degradation of the IRS1/2 proteins. This activity leads to long lasting inhibition of the IGF-1R pathway, growth inhibition of a wide range of cancer cell types, and potent anti-tumor effects. Thus, in another embodiment, the present invention provides a method of inhibiting, treating or preventing an insulin-like growth factor 1 receptor (IGF-1R) and/or insulin receptor substrate 1 (IRS1) and/or insulin receptor substrate 2 (IRK) signaling related disorder in a subject comprising the step of administering to said subject a pharmaceutical composition comprising a therapeutically effective amount of at least one compound represented by the structure of formula 1 or at least one of compounds 2-9. In some embodiments, the compound of formula (1) is an inhibitor of an insulin receptor or an insulin-like growth factor-1 receptor (IGF-1R) signaling, and/or the compound of formula (1) interacts with, affects or inhibits a substrate protein in the IGF-1R mediated pathway. In some embodiments, the substrate protein is Insulin Receptor Substrate 1 (IRS1), Insulin Receptor Substrate 2 (IRK), or a combination thereof. In one particular embodiment, the compound of formula (1) is an IGF-1R kinase inhibitor that leads to at least one of the dissociation of IRS1 or IRS2 from the cell membrane, phosphorylation of IRS1 or IRS2, and/or degradation of IRS1 or IRK, in any order.

The terms "interacts with, affects or inhibits" includes, without limitation, post-translational modifications, phosphorylation, translocation, and degradation, where such effects may be direct, i.e., by direct interaction of the compound of formula 1, or indirectly. e.g., through another protein or proteins.

In particular embodiments, the present invention provides a method of inhibiting, treating or preventing a protein kinase (PK) related disorder wherein the PK related disorder is selected from a cell proliferative disorder, a metabolic disorder, an inflammatory disorder, and a fibrotic disorder. Each possibility represents a separate embodiment of the present invention. In a currently preferred embodiment, the PK related disorder is cancer. In specific embodiments, the cancer is selected from the group consisting of ovarian cancer, prostate cancer, breast cancer, skin cancer, melanoma, metastatic melanoma, colon cancer, lung cancer, pancreatic cancer, gastric cancer, bladder cancer, Ewing's sarcoma, osteosarcoma, glioblastoma, lymphoma, leukemia, multiple myeloma, head and neck cancer, brain cancer, kidney cancer, bone cancer, liver cancer, hepatocarcinoma and thyroid cancer. Each possibility represents a separate embodiment of the present invention.

Within the scope of the present invention are pharmaceutical compositions comprising at least one compound represented by the structure of formula 1 or at least one of compounds 2-9 for inhibiting, treating or preventing a protein kinase (PK) related disorder in a subject. In various embodiments, the pharmaceutical compositions of the present invention are useful in inhibiting, treating or preventing an insulin-like growth factor 1 receptor (IGF-1R) and/or insulin receptor substrate 1 (IRS1) and/or insulin receptor substrate 2 (IRS2) signaling related disorder. In certain embodiments, the present invention provides a compound represented by the structure of formula 1 or any of compounds 2-9 for use in inhibiting, treating or preventing a protein kinase (PK) related disorder in a subject. In other embodiments, the compound represented by the structure of formula 1 or any of compounds 2-9 are useful in treating or preventing an insulin-like growth factor 1 receptor (IGF-1R) and/or insulin receptor substrate 1 (IRS1) and/or insulin receptor substrate 2 (IRS2) signaling related disorder. In some embodiments, the present invention provides a compound represented by the structure of formula 1 or any of compounds 2-9 for use in inhibiting, treating or preventing a disorder selected from the group consisting of a cell proliferative disorder, a metabolic disorder, an inflammatory disorder and a fibrotic disorder. Each possibility represents a separate embodiment of the present invention. In one embodiment, the present invention provides a compound represented by the structure of formula 1 or any of compounds 2-9 for use in inhibiting, treating or preventing cancer.

In some embodiments, the present invention provides a pharmaceutical composition comprising a compound represented by the structure of formula 1 or any of compounds 2-9 in combination with at least one other anti-cancer agent, wherein the compound and the at least one other anti-cancer agent together provide a therapeutic anti-cancer effect which is at least additive.

The present invention further provides a method of treating cancer or of inhibiting, treating or preventing a protein kinase (PK) related disorder comprising administering to the subject in need thereof a therapeutically effective amount of a compound represented by the structure of formula 1 or any of compounds 2-9 in combination with at least one other anti-cancer agent, wherein the compound and the at least one other anti-cancer agent together provide a therapeutic anti-cancer effect which is at least additive.

The present invention further provides the use of a compound represented by the structure of formula 1 or any of compounds 2-9 in combination with at least one other anti-cancer agent, wherein the compound and the at least one other anti-cancer agent together provide a therapeutic anti-cancer effect which is at least additive, for treating cancer or for inhibiting, treating or preventing a protein kinase (PK) related disorder.

The term "in combination" or "combined treatment" as used herein denotes any form of concurrent or parallel treatment with at least two distinct therapeutic agents. This term is intended to encompass both concomitant administration of the two treatment modalities, i.e., using substantially the same treatment schedule, as well as overlapping administration in sequential or alternating schedules of each treatment. Each possibility represents a separate embodiment of the present invention.

The compound represented by the structure of formula 1 or any of compounds 2-9 and the at least one other anti-cancer agent can be administered simultaneously (in the same or in separate dosage forms), or they can be administered sequentially, in any order. The administration can also take place according to alternating dosing schedules, e.g., the compound of the present invention followed by the at least one other anti-cancer agent, then an additional dose of the compound of the present invention, followed by the same or yet another anti-cancer agent and so forth. All administration schedules, including simultaneous, sequential and alternating, are contemplated by the present invention, wherein each possibility represents a separate embodiment of the present invention.

In one embodiment, the compound of the present invention and the at least one other anti-cancer agent together provide a therapeutic anti-cancer effect which is synergistic.

In some embodiments, the at least one anti-cancer agent is selected from an alkylating agent, an antibiotic agent, an anti-metabolic agent, an hormonal agent, a plant-derived agent and their synthetic derivatives, an anti-angiogenic agent, a differentiation inducing agent, a cell growth arrest inducing agent, an apoptosis inducing agent, a cytotoxic agent, an agent which affects cell bioenergetics i.e., which affects cellular ATP levels and molecules/activities regulating these levels, a biologic agent, e.g., a monoclonal antibody, a kinase inhibitor and a growth factor inhibitor and their receptors, a gene therapy agent, a cell therapy agent, e.g., stem cells, or any combination thereof. Each possibility represents a separate embodiment of the present invention.

In particular embodiments, the at least one other anti-cancer agent is selected from the group consisting of a protein kinase inhibitor, a proteasome inhibitor, a topoisomerase inhibitor, and an alkylating agent. Each possibility represents a separate embodiment of the present invention.

In some embodiments, the protein kinase inhibitor is selected from EGFR and/or HER2 inhibitors (e.g. small molecules such as genifitib, erlotinib and lapatinib or antibodies such as trastuzumab and cetuximab), B-Raf inhibitors (e.g. PLX-4032 and sorafenib), BCR-ABL and/or Src kinase inhibitors (e.g. imatinib, dasatinib and nilotinib), and VEGFR/PDGFR and/or multi kinase inhibitors (e.g. bevacizumab, sorafenib, sunitinib and pazopanib). Each possibility represents a separate embodiment of the present invention. In one embodiment, the protein kinase inhibitor is sorafenib.

In another embodiment, the proteasome inhibitor is bortezomib (PS-341, Velcade®). In other embodiments, the topoisomerase inhibitor is irinotecan. In further embodiments, the alkylating agent is dacarbazine or cisplatin. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 6 further shows the effect of compounds 2-5 on cell death, indicated by PARP cleavage, following 48 hr treatment with these compounds (FIGS. 6A&B). The same is demonstrated for 4 hr treatment with compound 5 and further incubation without the compound (FIG. 6C).

DETAILED DESCRIPTION OF THE INVENTION

Figure 1:
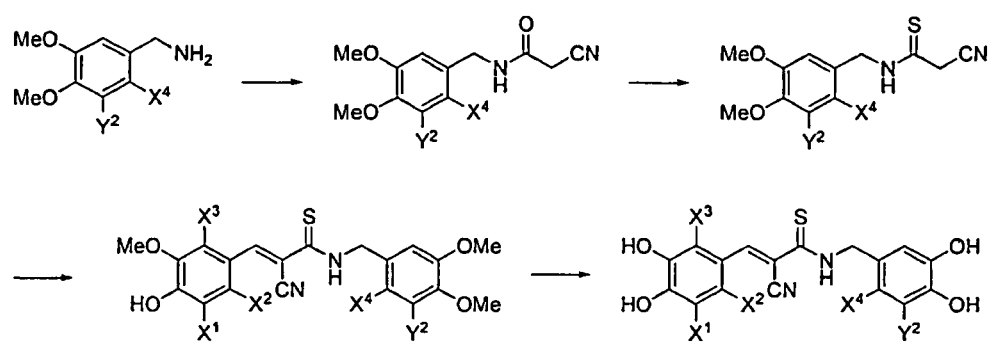
FIG. 1 Shows in schematic form a process for the synthesis of a precursor of formula (B) wherein $Y^1$, $Y^3$ and $Y^4$ are each OH; and A is CN.

The present invention relates to compounds which are potent inhibitors of PK activity, activation and signaling. The compounds are useful in treating or preventing PK-related disorders, particularly those which are associated with defects in signaling pathways mediated by PKs including various types of cancers and psoriasis.

The Insulin-like growth factor 1 receptor (IGF-1R) pathway is pivotal in many human malignancies. IGF-1R signaling is almost exclusively mediated by Insulin Receptor Substrates—IRS1 and IRS2. A number of IGF-1R kinase inhibitors and antibodies against IGF-1R have been shown to possess anti-tumor activity. The present invention is based in part on the unexpected discovery of a unique family of IGF-1R kinase inhibitors that lead to at least one of the following: the dissociation of IRS1/2 from the cell membrane, inhibitory serine phosphorylation of IRS1/2; and irreversible degradation of the IRS1/2 proteins. This leads to long lasting inhibition of the IGF-1R pathway, growth inhibition of a wide range of cancer cell types, and potent anti-tumor effects on a variety of cancers as exemplified herein.

The present invention thus provides compounds that are represented by the general structure of formula 1:

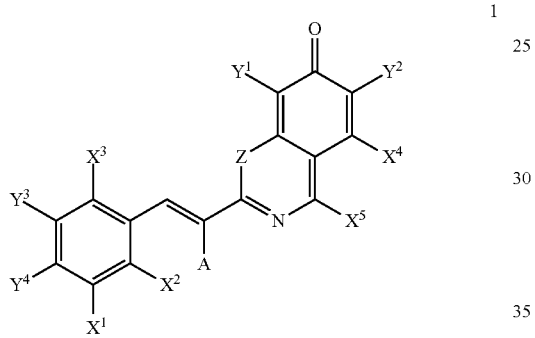

wherein
A is H or CN;
Z is S, SO or $SO_2$;
$X^1$, $X^2$, $X^3$, $X^4$, $X^5$, $Y^1$ and $Y^2$ are each independently selected from H, halogen, alkyl, haloalkyl and $OR^1$; and $Y^3$ and $Y^4$ are each $OR^1$, wherein each $R^1$ is independently H, $C_1$-$C_4$ alkyl, —$(CH_2CH_2O)_n$—, wherein n is an integer of 1 to 20, acyl or a functional group that gives rise to hydroxyl upon hydrolysis, including salts, hydrates, solvates, polymorphs, optical isomers, geometrical isomers, enantiomers, diastereomers, and mixtures thereof.

The present invention further provides compounds represented by the structure of formula 1 comprising any one or more of the following substitutions:
1. A is H.
2. A is CN.
3. Z is S.
4. Z is $SO_2$.
5. At least one of $X^1$, $X^2$, $X^3$, $X^4$, $Y^1$ and $Y^2$ is a halogen.
6. $Y^3$ and $Y^4$ are each OH.
7. $Y^1$ and $Y^2$ are each OH.
8. A is H or CN, Z is S, $Y^3$ and $Y^4$ are each OH, and $X^1$ is Br or I.
9. A is H, Z is S, $Y^3$ and $Y^4$ are each OH, and $X^3$ is Br or I.
10. A is H, Z is S, $Y^3$ and $Y^4$ are each OH, and $X^2$ is Br or I.
11. A is H, Z is S, $Y^3$ and $Y^4$ are each OH, and $X^1$ and $X^4$ are each Br or I.
12. $X^1$, $X^2$, $X^3$, and $X^4$ are each selected from H or a halogen.
13. A is H, Z is $SO_2$, $Y^3$ and $Y^4$ are each OH, and $X^1$ is a halogen selected from Br and I.
14. A is H, Z is $SO_2$, $Y^3$ and $Y^4$ are each OH, and at least one of $X^1$, $X^2$, $X^3$, $X^4$, $Y^1$ and $Y^2$ is a halogen.
15. $X^2$ is H.
16. $X^5$ is H.
17. $X^5$ is alkyl, preferably methyl.

Representative and non-limiting examples of such structures are compounds selected from the group consisting of compounds 2-9:

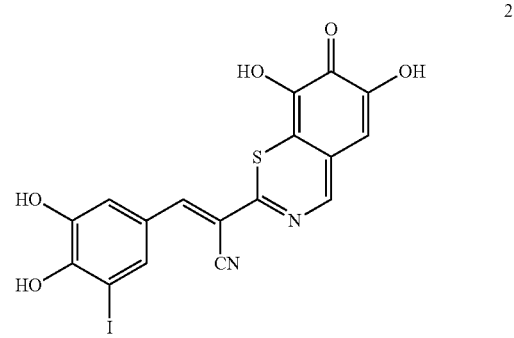

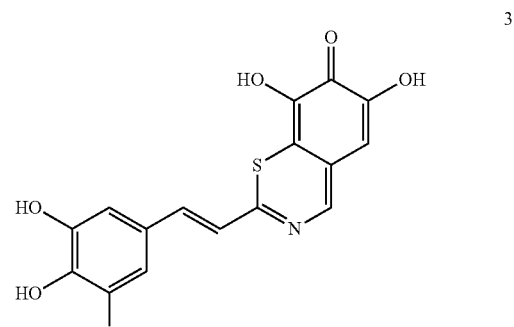

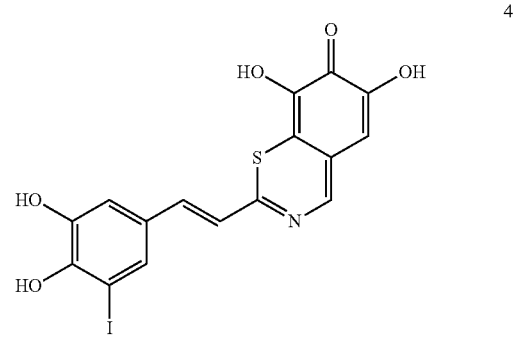

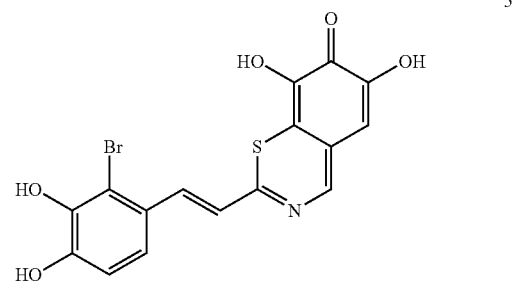

-continued

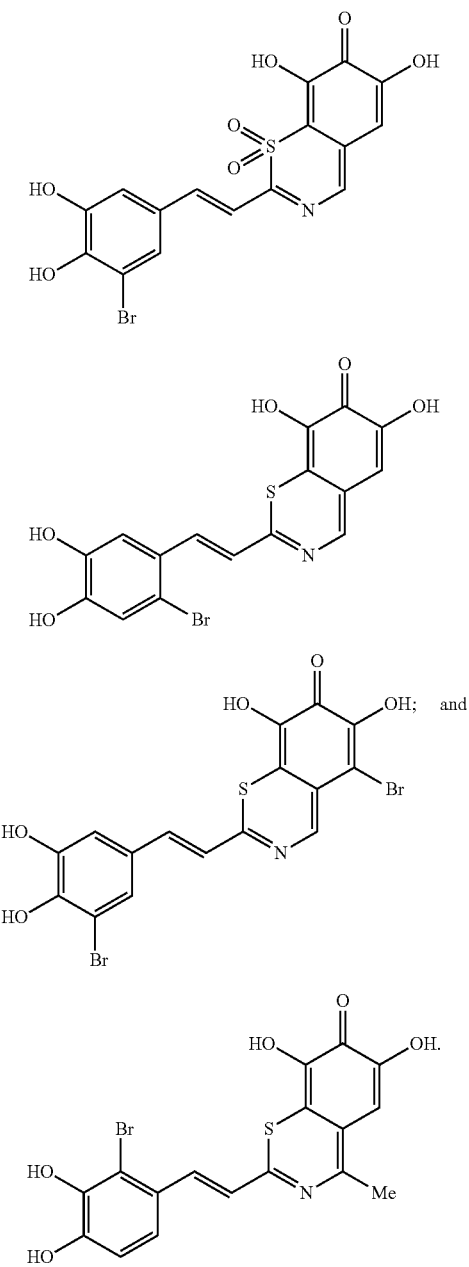

Although formulas 1-9 are drawn in a particular configuration, it is contemplated that the present invention encompasses all structural and geometrical isomers of such compounds, including cis, trans, E and Z isomers and optical isomers, and mixtures thereof, independently at each occurrence.

Chemical Definitions

The term "alkyl" as used herein refers to any saturated aliphatic hydrocarbon, including straight-chain, branched-chain and cyclic alkyl groups. In one embodiment, the alkyl group has 1-1.2 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl (e.g., methyl, ethyl, propyl, isopropyl, n-butyl, sec-butyl and t-butyl). The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

The term "acyl" as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

The term "halogen" or "halo" as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

Examples of functional groups that give rise to hydroxyl upon hydrolysis include, but are not limited to, esters, anhydrides, carbamates, carbonates and the like. For example, when $R^1$ is an acyl group (COR), the resulting functional group is an ester (OCOR). When $R^1$ is an amide group (CONHR), the resulting functional group is a carbamate (OCONHR). When $R^1$ is a carboxylate group (COOR), the resulting functional group is a carbonate (OCOOR).

All stereoisomers of the compounds of the present invention are contemplated, either in admixture or in pure or substantially pure form. These compounds can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. In addition, several of the compounds of the present invention contain one or more double bonds. The present invention intends to encompass all structural and geometrical isomers including cis, trans, E and Z isomers and optical isomers, independently at each occurrence.

One or more of the compounds of the invention, may be present as a salt. The term "salt" encompasses both basic and acid addition salts, including but not limited to carboxylate salts or salts with amine nitrogens, and include salts formed with the organic and inorganic anions and cations discussed below. Further encompassed by the term are salts formed by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like.

The term "organic or inorganic cation" refers to counter-ions for the carboxylate anion of a carboxylate salt. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.* (1977), 66:1-19, which is incorporated herein by reference. Other cations encompassed by the above term include the protonated form of procaine, quinine and N-methylglucosamine. Furthermore, any zwitterionic form of the instant compounds formed by a carboxylic acid and an amino group is also contemplated.

The present invention also includes solvates of any of compounds represented by formula 1 or any of compounds 2-9 and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of any of compounds represented by formula 1 or any of compounds 2-9 and salts thereof. The term "polymorph" refers to a particular crystalline state of a substance, which can be characterized by particular physical properties such as X-ray diffraction, IR spectra, melting point, and the like.

Therapeutic Use

The present invention provides compounds and compositions comprising compounds effective in modulating protein kinase signaling. These compounds and compositions are potentially useful in the treatment of diseases associated with altered or abnormal activity or signaling of protein kinases such as enhanced activity or signaling of protein kinases.

Thus, in one embodiment, the present invention provides a method of inhibiting signal transduction mediated by a protein kinase (PK) in a cell comprising contacting the cell with an effective inhibitory amount of at least one compound represented by the structure of formula 1, or at least one compound selected from compounds 2-9, or a pharmaceutical composition comprising one or more of such compounds as an active ingredient.

In another embodiment, the present invention provides a method of inhibiting cell proliferation comprising contacting the cell with an effective inhibitory amount of at least one compound represented by the structure of formula 1 or at least one compound selected from compounds 2-9.

The present invention further provides a method of inhibiting, treating or preventing a protein kinase (PK) related disorder in a subject comprising the step of administering to the subject a therapeutically effective amount of at least one compound represented by the structure of formula 1, or at least one compound selected from compounds 2-9. In another embodiment, the method comprises administering to the subject a pharmaceutical composition comprising a therapeutically effective amount of at least one compound represented by the structure of formula 1, or at least one compound selected from compounds 2-9 and a pharmaceutically acceptable carrier or excipient.

The present invention further provides a method of inhibiting, treating or preventing an insulin-like growth factor 1 receptor (IGF-1R) and/or insulin receptor substrate 1 (IRS1) and/or insulin receptor substrate 2 (IRS2) signaling related disorder in a subject comprising the step of administering to the subject a therapeutically effective amount of at least one compound represented by the structure of formula 1, or at least one compound selected from compounds 2-9. In another embodiment, the method comprises administering to the subject a pharmaceutical composition comprising a therapeutically effective amount of at least one compound represented by the structure of formula 1, or at least one compound selected from compounds 2-9; and a pharmaceutically acceptable carrier or excipient.

The present invention further provides the compound represented by the structure of formula 1 or any of compounds 2-9 for use in inhibiting, treating or preventing a protein kinase (PK) related disorder in a subject. The compounds are also useful for treating or preventing an insulin-like growth factor 1 receptor (IGF-1R) and/or insulin receptor substrate 1 (IRS1) and/or insulin receptor substrate 2 (IRS2) signaling related disorder. A compound represented by the structure of formula 1 or any of compounds 2-9 are further useful for inhibiting signal transduction mediated by a protein kinase (PK). Additionally, these compounds are useful for inhibiting cell proliferation.

The pharmaceutical compositions comprising at least one compound represented by the structure of formula 1 or at least one compound selected from compounds 2-9 in therapeutically effective amount and a pharmaceutically acceptable carrier or excipient are useful for inhibiting, treating or preventing a disorder selected from of a cell proliferative disorder, a metabolic disorder, an inflammatory disorder and a fibrotic disorder. Each possibility represents a separate embodiment of the present invention. In one embodiment, the pharmaceutical compositions are useful for inhibiting, treating or preventing cancer and for inhibiting cell proliferation.

A "protein kinase" (PK) is a protein belonging to a family of enzymes that transfer the γ-phosphate of ATP and covalently attaching it to one of three amino acids that have a free hydroxyl group on substrate proteins. Most kinases act on both serine and threonine, others act on tyrosine, and a number (dual specificity kinases) act on all three. PKs are involved in a variety of key cellular processes, including signal transduction and growth regulation. A protein kinase, as used herein, refers to a receptor kinase (RK) as well as a cellular kinase (CK or non-receptor kinase). Thus, the compounds of the present invention are effective at inhibiting both receptor and non-receptor protein kinases or signaling thereof.

A cellular tyrosine kinase (CTK or non-receptor tyrosine kinase) is an intracellular protein which takes part in signal transduction within the cell, including signal transduction to the nucleus. Examples of CTKs are the Src family of oncoproteins. A receptor tyrosine kinase (RTK) is a transmembrane protein that participates in transmembrane signaling pathways. The predominant biological activity of some receptor tyrosine kinases is the stimulation of cell growth and proliferation, while other receptor tyrosine kinases are involved in arresting growth and promoting differentiation. RTKs include, but are not limited to, the receptors for platelet-derived growth factor (PDGF), fibroblast growth factor (FGF), hepatocyte growth factor (HGF), insulin, insulin-like growth factor-1 (IGF-1), nerve growth factor (NGF), vascular endothelial growth factor (VEGF), and macrophage colony stimulating factor (M-CSF).

The term "protein kinase related disorder" as used herein refers to a disorder characterized by abnormal or altered PK activity or signaling. Abnormal or altered activity or signaling further refers to either (i) increased or decreased PK activity or levels leading to aberrant cell proliferation, differentiation and/or growth; or (ii) any increase or decrease in the activity or levels of molecules downstream to the PK resulting in aberrant signaling of said PK. Over-activity of PKs refers to either overexpression of said PK in cells that do not normally express PKs, or increased PK expression leading to unwanted cell proliferation, differentiation and/or growth. Furthermore, over-activity of PKs can also refer to amplification of the gene encoding a particular PK or production of a level of PK activity which can correlate with cell proliferation, differentiation and/or growth. Over-activity can also be the result of ligand independent or constitutive activation as a result of mutations such as deletions of a fragment of a PK responsible for ligand binding. Over-activity can also be the result of deregulation of ligand levels and availability for binding and regulating the PK activity. Alternatively, aberrant increased or decreased PK activity can result from loss of upstream regulation of said PK, changes in PK localization or its interactions with additional signaling molecules. In addition, decreased PK expression can lead to unwanted reductions in cell proliferation, differentiation and/or growth. As defined above, the disorder may further be characterized by abnormal or altered signal transduction mediated by a PK. Abnormal or altered signaling further refers to changes in the activity or levels of molecules downstream to the PK resulting in aberrant signaling mediated by said PK (e.g. an increase or decrease in the activity of IRS1/IRS2 leading to aberrant IGF-1R signaling).

Thus, in one embodiment, the present invention is directed to preparations containing at least one compound represented by the structure of formula 1, or at least one compound selected from compounds 2-9, which modulate PK activity signal transduction by affecting the activity of the protein kinases and interfering with the signal transduction pathways mediated by such proteins.

Examples of protein kinase related disorders are cell proliferative disorders, metabolic disorders or fibrotic disorders and inflammation.

Examples of cell proliferative disorders which are mediated by protein kinase activity, activation or signaling are cancer, psoriasis, diabetic nephropathy, blood vessel proliferative disorders, and mesangia cell proliferative disorders.

Cancer is a disorder in which a population of cells has become, in varying degrees, unresponsive to the control mechanisms that normally govern proliferation and differentiation. Cancer refers to various types of malignant neoplasms and tumors, including metastasis to different sites. Non-limiting examples of cancers which can be treated by any of the compounds represented by the structure of formula 1, or any of the compounds 2-9 are brain, ovarian, colon, prostate, hepatic, pancreatic, kidney, bladder, breast, lung, oral, and skin cancers. Specific examples of cancers are: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, metastatic melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, glioblastoma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, and non-Hodgkin's lymphoma. Each possibility represents a separate embodiment of the present invention.

According to certain embodiments, the cancer to be treated is selected from the group consisting of prostate cancer, breast cancer, skin cancer (including melanoma), metastatic melanoma, colon cancer, lung cancer, pancreatic cancer, lymphoma, myeloma, leukemia (including lymphoblastic leukemia), head and neck cancer, kidney cancer, ovarian cancer, vaginal tumor, stomach cancer, larynx cancer, bone cancer, liver cancer or thyroid cancer. Each possibility represents a separate embodiment of the present invention.

The present invention further provides a method of inhibiting, treating or preventing an insulin-like growth factor 1 receptor (IGF-1R) and/or insulin receptor substrate 1 (IRS1) and/or insulin receptor substrate 2 (IRS2) signaling related disorder. Data from experimental models and population studies have implicated that the IGF-1 system is involved in the pathogenesis of many different human cancers, including breast, prostate, lung, and colon cancer (reviewed in Ryan et al., *The Oncologist* (2008), 13: 16-24). There are also several lines of evidence that dysregulation of the IGF-1 system and enhanced IGF-1R activation are involved in resistance to certain anticancer therapies, including cytotoxic chemotherapy, hormonal agents, biological therapies, and radiation.

Insulin receptor substrate 1 (IRS-1) is a constituent of the IGF-1R signaling pathway, and has been shown to be a key mediator in its role in malignant transformation (reviewed in Baserga, *Exp. Cell Res*. (2009), 315(5): 727-732).

Without wishing to be bound by any particular mechanism or theory, it is contemplated that the compounds disclosed herein are useful as inhibitors of IGF-1R signaling and/or IRS-1 and/or IRS-2 signaling thus being highly potent in treating or preventing different types of cancer, both as a single agent therapeutic, and as an enhancement of existing therapies. Inhibition of IRS-1 signaling is beneficial for the treatment of various cancers where IGF-1R has been shown to be involved, as well as for the treatment of other types of cancers, which are independent of IGF-1R. In some embodiments, the present invention is directed to compounds that are IGF-1R kinase inhibitors, that trigger any one or more of the following, in any order: (i) serine phosphorylation of the IGF-1R direct substrates IRS1 and/or IRS2; (ii) dissociation of IRS1 and/or IRS2 from the cell membrane; and/or (iii) degradation of IRS1 and/or IRS2, thus providing long-lasting effects which enhance the inhibitory activity of these novel compounds.

The term "treating" as used herein refers to abrogating, inhibiting, slowing or reversing the progression of a disease, ameliorating clinical symptoms of a disease or preventing the appearance of clinical symptoms of a disease. The term "preventing" is defined herein as barring a subject from acquiring a disorder or disease.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastasis, reduction in the number of new metastasis formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of tumor regression, and the like.

The term "administering" as used herein refers to bringing into contact with a compound of the present invention thus affecting the activity, activation or signaling of the kinase either directly; i.e. by interacting with the kinase itself, or indirectly; i.e. by interacting with another molecule on which the signaling activity of the enzyme is dependent. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The term "inhibition of cell proliferation" as used herein refers to inhibition of abnormal cells preferably cancerous cells expressed as a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

The term "therapeutically effective amount" refers to the amount of a compound being administered which provides a therapeutic effect for a given condition and administration regimen, specifically an amount which relieves to some extent one or more of the symptoms of the disorder being treated. Therapeutic effective doses for any compounds represented by the structure of formula 1, or any of the compounds 2-9 described herein can be estimated initially from cell culture and/or an animal model. A dose can be formulated in an animal model, and this dose can be used to more precisely determine useful doses in humans.

The term "effective inhibitory amount" refers to the amount of a compound being administered that inhibits to some extent the protein kinase with which it is contacted.

Pharmaceutical Compositions:

The present invention further provides pharmaceutical compositions comprising at least one compound represented by the structure of formula 1, or at least one compound selected from compounds 2-9, and a pharmaceutically acceptable carrier or excipient. As used herein, "pharmaceutical composition" means therapeutically effective amounts of the compounds of the present invention, together with suitable diluents, preservatives, solubilizers, emulsifiers, adjuvant and/or carriers. Such compositions are liquids or lyophilized or otherwise dried formulations and include diluents of various buffer content (e.g., Tris-HCI, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further contemplated by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. In one embodiment, the pharmaceutical composition is administered parenterally, paracancerally, transmucosally, transdermally, intramuscularly, intravenously, intradermally, subcutaneously, intraperitonealy, intraventricularly, intracranially or intratumorally.

Moreover, as used herein "pharmaceutically acceptable carriers" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also contemplated by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see for example Saudek et al., *N Engl. J. Med.* (1989), 321:574-579). In another embodiment, polymeric materials can be used. In yet another embodiment, a controlled release system can be placed in proximity to the therapeutic target, i.e., the brain, thus requiring only a fraction of the systemic dose (see, e.g., Goodson, *Medical Applications of Controlled Release*, supra (1984), 2:115-138). Preferably, a controlled release device is introduced into a subject in proximity to the site of inappropriate immune activation or a tumor. Other controlled release systems are discussed in the review by Langer, *Science* (1990), 249: 1527-1533.

The pharmaceutical preparation may comprise one or more of the compounds represented by the structure of formula 1, or any of the compounds 2-9, or may further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the receptor modulator can be administered to a subject by, for example, subcutaneous implantation of a pellet; in a further embodiment, the pellet provides for controlled release of receptor modulator over a period of time. The preparation can also be administered by intravenous, intra-arterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the receptor modulators or their physiologically tolerated derivatives such as salts, esters, N-oxides, and the like are mixed with additives customary for this purpose, such as vehicles, stabilizers, or inert diluents, and converted by customary methods into a suitable form of administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, or with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the compounds of the present invention or their physiologically tolerated derivatives such as salts, hydrates and the like are converted into a solution, suspension, or emulsion, if desired with the substances customary and suitable for this purpose, for example, solubilizers or other auxiliaries. Examples are sterile liquids such as water and oils, with or without the addition of a surfactant, and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycols are preferred liquid carriers, particularly for injectable solutions.

The preparation of pharmaceutical compositions which contain an active component is well understood in the art. Typically, such compositions are prepared as aerosols of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as wetting or emulsifying agents, pH buffering agents, which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the compounds of the present invention or their physiologically tolerated derivatives such as salts, hydrates, and the like are prepared and applied as solutions, suspensions, or emulsions in a physiologically acceptable diluent with or without a pharmaceutical carrier.

In another embodiment, the active compound can be delivered in a vesicle, in particular a liposome (see for example Langer, *Science* (1990), 249: 1527-1533; Treat et al., *Liposomes in the Therapy of Infectious Disease and Cancer* (1989), Lopez-Berestein and Fidler (eds.), Liss, N.Y., 353-365).

Combination Therapy:

The present invention further provides compositions and methods for treating cancer or for inhibiting, treating or preventing a protein kinase (PK) related disorder, by administering a combination comprising a compound represented by the general structure of formula 1, or any compound encompassed by this generic structure including, but not limited to, any of compounds 2, 3, 4, 5, 6, 7, 8 or 9 in combination with at least one other anti-cancer agent. In some embodiments, the compound of the present invention and the at least one other anti-cancer agent are administered in an amount which provides a therapeutic anti-cancer effect which is at least additive. In other embodiments, the compound of the present invention and the at least one other anti-cancer agent are administered in an amount which provides a therapeutic anti-cancer effect which is synergistic.

Cancers treated with conventional radio- or chemo-therapy or other anti-cancer agents frequently develop resistance to these treatments, ultimately leading to recurrent disease that often has a more aggressive phenotype than that observed at the time of the original diagnosis (Li et al., J. Med. Chem. (2009), 52(16): 4981-5004). Combinations of drugs from different categories are useful to prevent or overcome emergence of drug resistant tumors. The combination therapy can further provide a therapeutic advantage in view of the differential toxicity associated with the two individual treatments. For example, treatment with a compound of the present invention can lead to a particular toxicity that is not seen with the at least one other anti-cancer agent, and vice versa. As such, this differential toxicity can permit each treatment to be administered at a dose at which said toxicities do not exist or are minimal, such that together the combination therapy provides a therapeutic dose while avoiding the toxicities of each of the constituents of the combination agents. Furthermore, when the therapeutic effects achieved as a result of the combination treatment are enhanced or synergistic, i.e., significantly better than additive therapeutic effects, the doses of each of the agents can be reduced even further, thus lowering the associated toxicities to an even greater extent.

The terms "synergistic", "cooperative" and "super-additive" and their various grammatical variations are used interchangeably herein. An interaction between a compound of the present invention and another anti-cancer agent is considered to be synergistic, cooperative or super-additive when the observed effect (e.g., cytotoxicity) in the presence of the drugs together is higher than the sum of the individual effects of each drug administered separately. In one embodiment, the observed combined effect of the drugs is significantly higher than the sum of the individual effects. The term significant means that the observed $p<0.05$. A non-limiting manner of calculating the effectiveness of the combined treatment comprises the use of the Bliss additivism model (Cardone et al. Science (1998), 282: 1318-1.321) using the following formula: Ebliss=EA+EB−EA×EB, where EA and EB are the fractional inhibitions obtained by drug A alone and drug B alone at specific concentrations. When the experimentally measured fractional inhibition is equal to Ebliss, the combination provides an additive therapeutic effect. When the experimentally measured fractional inhibition is greater than Ebliss, the combination provides a synergistic therapeutic effect.

The anti-cancer treatments for use in the combinations of the present invention include radiation therapy, chemotherapy, immunotherapy, hormonal therapy and genetic therapy. Each possibility represents a separate embodiment of the present invention.

Suitable anti-cancer agents for use in the combinations of the present invention include, but are not limited to, alkylating agents, antibiotic agents, antimetabolic agents, hormonal agents, plant-derived agents, anti-angiogenic agents, differentiation inducing agents, cell growth arrest inducing agents, apoptosis inducing agents, cytotoxic agents, agents affecting cell bioenergetics, biologic agents, e.g., monoclonal antibodies, kinase inhibitors and inhibitors of growth factors and their receptors, gene therapy agents, cell therapy, e.g., stem cells, or any combination thereof. Each possibility represents a separate embodiment of the present invention.

In one embodiment, the at least one other anti-cancer agent is an alkylating agent. Alkylating agents are drugs which impair cell function by forming covalent bonds with amino, carboxyl, sulfhydryl and phosphate groups in biologically important molecules. The most important sites of alkylation are DNA, RNA and proteins. Alkylating agents depend on cell proliferation for activity but are not cell-cycle-phase-specific. Non-limiting examples of alkylating agents include bischloroethylamines, (nitrogen mustards, (e.g. chlorambucil, cyclophosphamide, ifosfamide, mechlorethamine, melphalan, uracil mustard), aziridines (e.g. thiotepa), alkyl alkone sulfonates (e.g. busulfan), nitroso-ureas (e.g. BCNU, carmustine, lomustine, streptozocin), non-classic alkylating agents (e.g., altretamine, dacarbazine, and procarbazine), and inorganic ions including platinum compounds (e.g., carboplatin, oxaloplatin and cisplatin). Each possibility represents a separate embodiment of the present invention. Currently preferred alkylating agents for use in the combinations of the present invention include cisplatin and dacarbazine. Each possibility represents a separate embodiment of the present invention.

In another embodiment, the at least one other anti-cancer agent is a protein kinase inhibitor. Protein kinase inhibitors are small molecules or antibodies which inhibit the phosphorylation of hydroxy groups on tyrosine, serine and threonine residues of proteins, thus affecting cell growth, differentiation and proliferation. Non-limiting examples of protein kinase inhibitors include EGFR and/or HER2 inhibitors (e.g. genifitib, erlotinib, lapatinib, trastuzumab and cetuximab), B-Raf inhibitors (e.g. PLX-4032 and sorafenib), BCR-ABL and/or Src family kinase inhibitors (e.g. imatinib, dasatinib and nilotinib), VEGFR/PDGFR and/or multi kinase inhibitors (e.g. bevacizumab, sorafenib, sunitinib and pazopanib). Each possibility represents a separate embodiment of the present invention.

In another embodiment, the at least one other anti-cancer agent is a proteasome inhibitor. Proteasome inhibitors have effective anti-tumor activity in cell culture, inducing apoptosis by disrupting the regulated degradation of pro-growth cell cycle proteins. Non-limiting examples of proteasome inhibitors include bortezomib (PS-341) and disulfuram. Each possibility represents a separate embodiment of the present invention.

In yet another embodiment, the at least one other anti-cancer agent is a topoisomerase inhibitor. Topoisomerase inhibitors are agents which interfere with the action of topoisomerase enzymes (topoisomerase I and II) that control the changes in DNA structure by catalyzing the breaking and rejoining of the phosphodiester backbone of DNA strands during the normal cell cycle. Non-limiting examples of topoisomerase inhibitors are irinotecan, topotecan, camptothecin, lamellarin D and etoposide. Each possibility represents a separate embodiment of the present invention. A currently preferred topoisomerase inhibitor is irinotecan.

In further embodiments, the at least one other anti-cancer agent is an anti-tumor antibiotics. Anti-tumor antibiotics like adriamycin intercalate DNA at guanine-cytosine and guanine-thymine sequences, resulting in spontaneous oxidation and formation of free oxygen radicals that cause strand breakage. Non-limiting examples of antibiotic agents include anthracyclines (e.g. doxorubicin, daunorubicin, epirubicin, idarubicin and anthracenedione), mitomycin C, bleomycin, dactinomycin, and plicatomycin. Each possibility represents a separate embodiment of the present invention.

In additional embodiments, the at least one other anti-cancer agent is an anti-metabolic agent. Anti-metabolic agents suitable for use in the present invention include, but are not limited to, 6-mercaptopurine, floxuridine, 5-fluorouracil, methotrexate, leucovorin, hydroxyurea, thioguanine, mercaptopurine, cytarabine, pentostatin, fludarabine phosphate, cladribine, asparaginase, and gemcitabine. Each possibility represents a separate embodiment of the present invention.

In further embodiments, the at least one other anti-cancer agent is a hormonal agent. Hormonal agents suitable for use in the present invention include, but are not limited to, an estrogen, a progestogen, an antiesterogen, an androgen, an antiandrogen, an LHRH analogue, an aromatase inhibitor, diethylstibestrol, tamoxifen, toremifene, fluoxymesterol, raloxifene, bicalutamide, nilutamide, flutamide, aminoglutethimide, tetrazole, ketoconazole, goserelin acetate, leuprolide, megestrol acetate, and mifepristone. Each possibility represents a separate embodiment of the present invention.

In some embodiments, the at least one other anti-cancer agent is a plant derived agent. Plant derived agents include, but are not limited to, taxanes, which are semisynthetic derivatives of extracted precursors from the needles of yew plants. These drugs have a novel 14-member ring, the taxane. The taxanes (e.g., taxol) promote microtubular assembly and stability, therefore blocking the cell cycle in mitosis. Other plant derived agents include, but are not limited to, vinca alkaloids including vincristine, vinblastine, vindesine, vinzolidine, vinorelbine, etoposide, teniposide, paclitaxel and docetaxel; podophyllotoxins including etoposide, irinotecan, and topotecan. Each possibility represents a separate embodiment of the present invention. In one embodiment, the plant derived agent is a jasmonate derivative (e.g. methyl jasmonate).

In certain embodiments, the at least one other anti-cancer agent is a biologic agent such as, but not limited to, immuno-modulating proteins, monoclonal antibodies against tumor antigens, tumor suppressor genes, kinase inhibitors and inhibitors of growth factors and their receptors and cancer vaccines. For example, the immuno-modulating protein can be interleukin 2, interleukin 4, interleukin 12, interferon El interferon D, interferon alpha, erythropoietin, granulocyte-CSF, granulocyte, macrophage-CSF, bacillus Calmette-Guerin, levamisole, or octreotide. Each possibility represents a separate embodiment of the present invention. Furthermore, the tumor suppressor gene can be DPC-4, NF-1, NF-2, RB, p53, WT1, BRCA, or BRCA2. Each possibility represents a separate embodiment of the present invention.

Recent developments have introduced, in addition to the traditional cytotoxic and hormonal therapies, additional therapies for the treatment of cancer. For example, many forms of gene therapy are undergoing preclinical or clinical trials. In addition, approaches are currently under development, such approaches are based on the inhibition of tumor vascularization (angiogenesis). The concept of treatment is based on the cut off the tumor from nutrition and oxygen supply provided by a newly built tumor vascular system. In addition, cancer therapy is also being attempted by the induction of terminal differentiation of the neoplastic cells. Suitable differentiation agents include, but are not limited to, hydroxamic acids, derivatives of vitamin D and retinoic acid, steroid hormones, growth factors, tumor promoters, and inhibitors of DNA or RNA synthesis. Each possibility represents a separate embodiment of the present invention. Also, histone deacetylase inhibitors are suitable chemotherapeutic agent to be used in the present invention.

Additional anti-cancer agents within the scope of the present invention are glycolytic inhibitors such as 2DG oxamate and its derivatives and the like, and other signal transduction inhibitors (small molecules, peptides or antibodies), which block the activation or inhibit the kinase activity of cKit, cRaf, Akt, and/or mTOR. Each possibility represents a separate embodiment of the present invention. In additional embodiments, the present invention provides the combination of the compound of the present invention with at least one other anti-cancer treatment. Anti-cancer treatments include radiation therapy (radiation oncology, radiotherapy) and surgery. Each possibility represents a separate embodiment of the present invention.

Specific compounds for chemotherapeutic treatment in combination with the compounds of the invention are selected from the group consisting of topoisomerase inhibitors, spindle poison vincas: vinblastine, vincristine, vinorelbine (taxol), paclitaxel, docetaxel; and alkylating agents: mechlorethamine, chlorambucil, cyclophosphamide, melphalan, ifosfamide; methotrexate; 6-mercaptopurine; 5-fluorouracil, cytarabine, gemcitabin; podophyllotoxins: etoposide, irinotecan, topotecan; anticancer chemicals containing a quinone group: carbazilquinone; antibiotics: doxorubicin (adriamycin), daunorubicin, idarubicin, epirubicin, bleomycin, mitomycin; nitrosoureas: carmustine (BCNU), lomustine; inorganic ions: cisplatin, carboplatin; interferon, asparaginase; hormones: tamoxifen, leuprolide, flutamide, and megestrol acetate, and dacarbazine. Each possibility represents a separate embodiment of the present invention. A table of approved anti-cancer drugs for various types of cancers suitable for use in the combinations of the present invention is attached as Appendix A.

The treatment with the compound of the present invention and the at least other anti-cancer agent can take place sequentially in any order, simultaneously or a combination thereof. For example, administration of a compound of the present invention can take place prior to, after or at the same time as administration of the other anti-cancer agent. For example, a total treatment period can be decided for the compound of the present invention. The additional agent(s) can be administered prior to onset of treatment with the compound or following treatment with the compound of the present invention. In addition, the additional agent(s) can be administered during the period of the administration of the compound of the present invention but does not need to occur over the entire treatment period. In another embodiment, the treatment regimen includes pre-treatment with one agent, either the compound of the present invention or the other ant-cancer agent, followed by the addition of the other agent or agents. Alternating sequences of administration are also contemplated. Alternating administration includes administration of a compound of the present invention, and another anti-cancer agent in alternating sequences, e.g., compound, followed by another anti-cancer agent, followed by the compound of the present invention, etc.

The combinations of the present invention may further comprise any of the conventional excipients such as stabilizers, tonicity modifiers, buffering agents, preservatives, disintegrating agents, diluents, binders, emulsifying agents, lubricants, wetting agents, and complexing agents as defined herein above.

It should be noted that the term "and" or the term "or" are generally employed in its sense including "and/or" unless the content clearly dictates otherwise.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

Example 1

Synthesis—General Procedure

The compounds of formula (I) can generally be prepared by oxidation of general precursors of formula (B) as set forth in the scheme below:

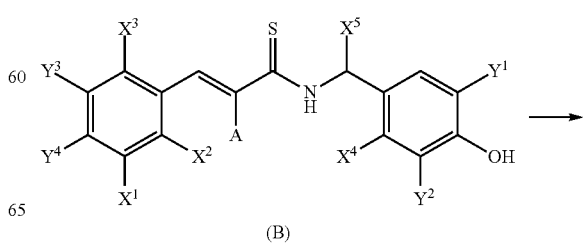

(B)

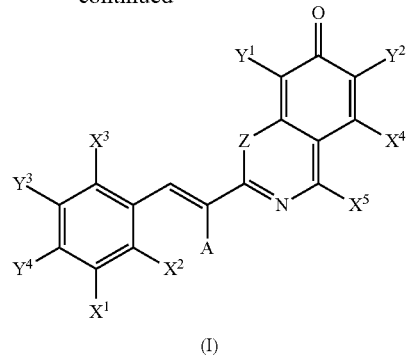

(I)

The precursor of formula (B) was reacted with an oxidizing agent, e.g., a mixture of $H_2NaPO_4$ and $HNa_2PO_4$. Following incubation, the product was centrifuged and the precipitate was washed with (2-N-morpholine)-ethane sulphonic acid (MES) and water, and lyophilized to give a compound of formula (I) wherein Z=S. Further oxidation to the sulfoxide (Z=SO) or sulfone (Z=$SO_2$) can be performed as known to a person of skill in the art.

This procedure is exemplified for the preparation of compounds of formula (3), (5), (2), (4), (7), (8) and (9):

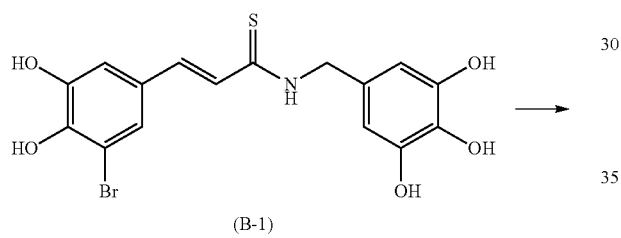

(B-1)

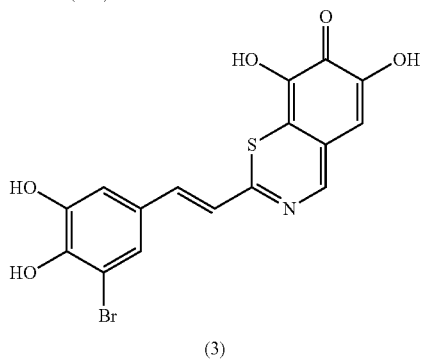

(3)

960 mg of precursor B-1 were dissolved in 10% ACN/DDW (4.8 lit). A mixture of 304 ml 0.2M $H_2NaPO_4$ and 1.3 ml 0.2M $HNa_2PO_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and lyophilized to give compound 3 as a black powder (90%). The purity of compound 3 was >99% as detected by HPLC and by elemental microanalysis.

The assignment of the proton NMR signals of compound 3 is as follows: $^1$H NMR (500 MHz, in DMSO-$d_6$): δ 8.25 (s, 1H), 7.71 (d, J=16 Hz, 1H), 7.51 (s, 1H), 7.15 (s, 1H), 7.12 (d, J=16 Hz, 1H), 6.80 (s, 1H). Represents only H atoms in C—H bonds. MS (ESI). found (m/z) 407.9. calculated for $C_{16}H_{10}BrNO_5S$ (MH$^+$) 407.95. Anal. ($C_{16}H_{10}BrNO_5S$) C, H, N, Br, S.

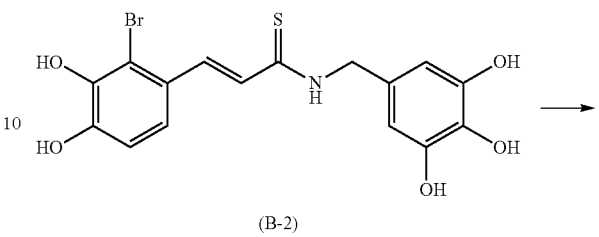

(B-2)

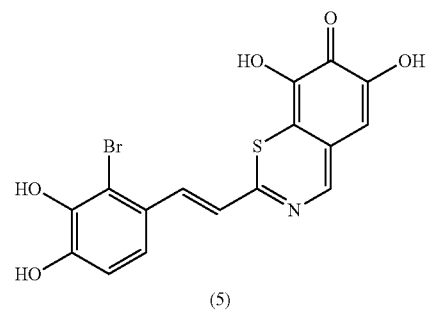

(5)

960 mg of precursor B-2 were dissolved in 10% ACN/DDW (4.8 lit). A mixture of 304 ml 0.2M $H_2NaPO_4$ and 1.3 L 0.2M $HNa_2PO_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and finally lyophilized to give compound 5 as a black powder (55%). Compound 5 was obtained as a hydrate containing 1.5 molecules of water. The purity of compound 5 was >99% as detected by HPLC and by elemental microanalysis.

The assignment of the proton NMR signals of compound 5 is as follows: $^1$H NMR (500 MHz, in DMSO-$d_6$): δ 8.25 (s, 1H), 8.12 (d, J=16 Hz, 1H), 7.45 (d, J=8 Hz, 1H), 7.17 (d, J=16 Hz 1H), 6.96 (s, 1H), 6.80 (d, J=8 Hz 1H). Represents only H atoms in C—H bonds. MS (ESI). found (m/z) 407.9. calculated for $C_{16}H_{10}BrNO_5S$ (MH$^+$) 407.95. Anal. ($C_{16}H_{10}BrNO_5S$) C, H, N, Br, S.

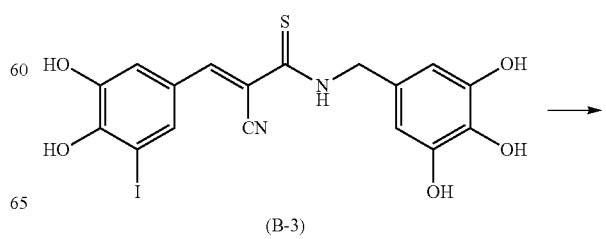

(B-3)

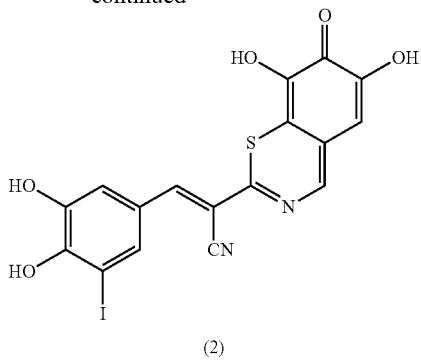

(2)

120 mg of precursor B-3 were dissolved in 10% ACN/DDW (1.2 lit). A mixture of 76 ml 0.2M H$_2$NaPO$_4$ and 325 ml 0.2M HNa$_2$PO$_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and finally lyophilized to give compound 2 as a dark brown powder (34%). The purity of compound 2 was 80% as detected by HPLC and by elemental microanalysis.

The assignment of the proton NMR signals of compound 2 is as follows:

$^1$H NMR (500 MHz, in DMSO-d$_6$): δ 8.20 (s, 1H), 8.07 (s, 1H), 8.03 (s, 1H), 7.71 (s, 1H), 6.95 (s, 1H). Represents only H atoms in C—H bonds. MS (ESI). found (m/z) 480.93. calculated for C$_{17}$H$_{10}$IN$_2$O$_5$S (MH$^+$) 480.93.

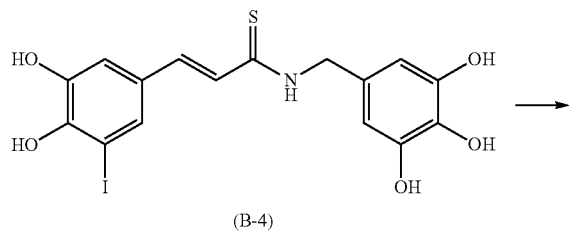

(B-4)

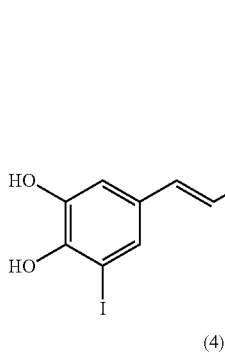

(4)

240 mg of precursor B-4 were dissolved in 10% ACN/DDW (1.2 lit). A mixture of 76 ml 0.2M H$_2$NaPO$_4$ and 325 ml 0.2M HNa$_2$PO$_4$ was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M IVIES (2-(N-morpholine)-ethane sulphonic acid) pH~5, then with DDW and finally lyophilized to give compound 4 as a black powder (55%). The crude product was obtained at 90% purity. Further purification was performed by dissolving and stirring crude compound 4 in 3 ml MeOH and 100 μL HCl 6N. After 20 minutes, the solution was filtered through silicagel 60, and neutralized to pH=7.5 with ammonium hydroxide. The dark precipitant obtained after 48 hours was filtered, washed with water and lyophilized. The purity of compound 4 was >99% as detected by HPLC and by elemental microanalysis.

The assignment of the proton NMR signals of compound 4 is as follows:

$^1$H NMR (500 MHz, in DMSO-d$_6$): δ 8.26 (s, 1H), 8.12 (d, J=16 Hz, 1H), 7.5 (d, J=1.5 Hz, 1H), 7.16 (d, J=1.5 Hz 1H), 7.09 (d, J=16, 1H), 6.99 (s, 1H). Represents only H atoms in C—H bonds. MS (ESI). found (m/z) 455.93. calculated for C$_{16}$H$_{10}$INO$_5$S (MO 455.93.

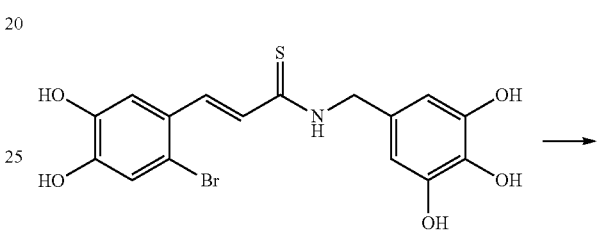

(B-5)

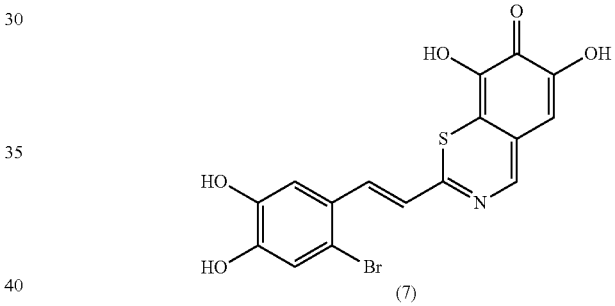

(7)

30 mg of precursor B-5 were dissolved in 10% ACN/DDW (8 ml). A mixture of 5 ml 0.2M H$_2$NaPO$_4$/HNa$_2$PO$_4$ buffer, pH=7.4 was added and the solution was stirred at room temperature for 1 hour, in which the solution changed its color from yellow to black. The reaction mixture was allowed to stay for at least 48 hours at 4° C. Following the incubation, the product was centrifuged. The precipitate was washed with 0.1M MES (2-(N-morpholine)-ethane sulphonic acid) pH~5, then with DDW and finally lyophilized to give compound 7 as a dark brown powder (30%). The purity of compound 7 was 70% as detected by HPLC.

MS (ESI). found (m/z) 407.95. calculated for C$_{16}$H$_{10}$BrNO$_5$S (MH$^+$) 407.95.

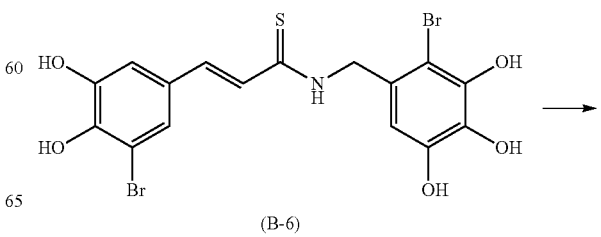

(B-6)

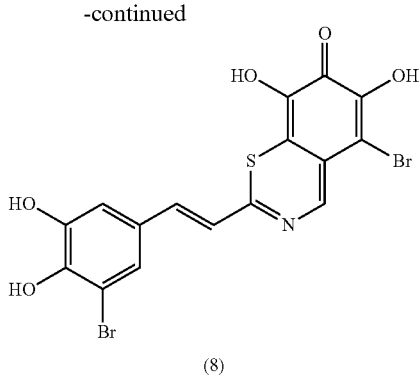

(8)

45 mg of precursor B-6 were dissolved in 10% ACN/DDW (2 ml). A mixture of 3 ml 0.2M H$_2$NaPO$_4$ and 12 ml 0.2M HNa$_2$PO$_4$ was added and the solution was stirred at room temperature for 1 hour. The reaction mixture was allowed to stand for at least 48 hours at 4° C. Following the incubation the product was centrifuged. The precipitate was washed with 0.1 M MES (2-(N-morpholine)-ethane sulphonic acid) pH~5, then with DDW and finally was lyophilized to give compound 8 as a dark brown powder (45%). The purity of compound 8 was 70% as detected by HPLC and NMR. Cleaning of compound 8 was performed by preparative HPLC, yielding 4 mg of 8, 80% purity according to HPLC and NMR.

The assignment of the proton NMR signals of compound 8 is as follows $^1$H NMR (500 MHz, in MeOH, $^4$d): δ 7.75 (d, J=6, 1H), 7.35 (s, 1H), 7.1 (s, 1H), 7.05 (dd, J=16, 0.7 Hz 1H), Represents only H atoms in C—H bonds. MS (ESI). found (m/z) 487.86 (MH$^+$). calculated for C$_{16}$H$_9$Br$_2$NO$_5$S (MH$^+$) 486.86.

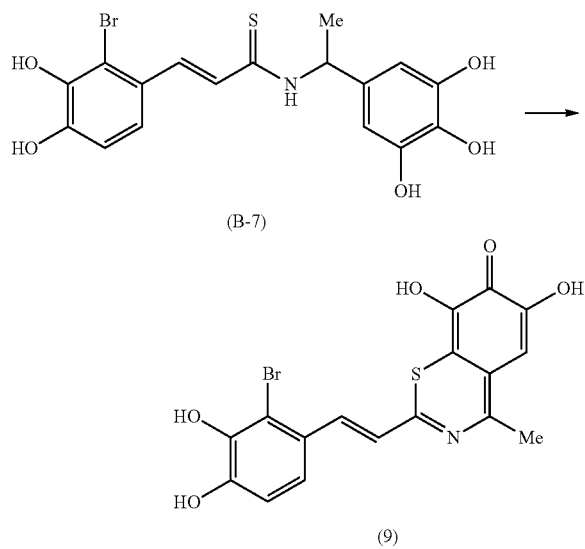

(B-7)

(9)

30 mg of precursor B-7 are dissolved in 10% ACN/DDW (10 ml). A mixture of 5 ml 0.2M H$_2$ KPO$_4$/HK$_2$PO$_4$ buffer, pH=7.4 is added and the solution stirred at room temperature for 1 hour, in which the solution changes its color from yellow to black. The reaction mixture is allowed to stay for at least 48 hours at 4° C. Following incubation the product is centrifuged. The precipitate is washed with 0.1M MES (2-(N-morpholine)-ethane sulphonic acid) pH~5, then with DDW and finally lyophilized to give compound 9 as a dark powder. The purity of compound 9 is detected by HPLC and NMR.

Other compounds of formula (I) may be prepared in the same manner from their corresponding precursors of formula (B).

Figure 2:
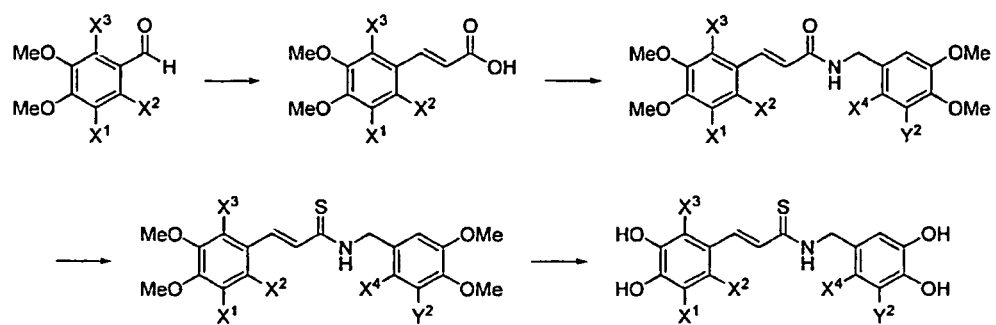
FIG. 2 Shows in schematic form a process for the synthesis of a precursor of formula (B) wherein $Y^1$, $Y^3$ and $Y^4$ are each OH; and A is H.

General procedures for the synthesis of compounds of formula (B) are further described in PCT international patent applications WO 2008/068751 and WO 2009/147682, the contents of each of which are incorporated by reference in their entirety. Some non-limiting examples are provided in FIGS. 1 and 2, and in the description below.

I. General Procedure for the Synthesis of Precursors of Formula (B) Wherein A=CN):

A. General Procedure for the Synthesis of the Following Intermediate Compound:

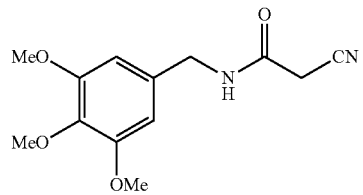 [SMILES: COc1cc(CNC(=O)CC#N)cc(OC)c1OC]

3,4,5-trimethoxybenzylamine (1.2 equiv) and methyl cyanoacetate (1 equiv) were stirred at room temperature until the precipitation of the product was observed. The product was collected by filtration, washed twice with ethanol, and dried under reduced pressure. The product was obtained as a white solid in 70-80% yield.

$^1$H NMR (300 MHz, in CDCl$_3$): δ 6.49 (s, 2H), 6.37 (bs, 1H), 4.40 (d, J=4.4 Hz, 2H), 3.86 (s, 6H), 3.84 (s, 3H), 3.43 (s, 2H). MS (ESI). found (m/z) 265.60. calculated for C$_{13}$H$_{17}$N$_2$O$_4$ (MH$^+$) 265.11.

B. General Procedure for the Synthesis of the Following Intermediate Compound:

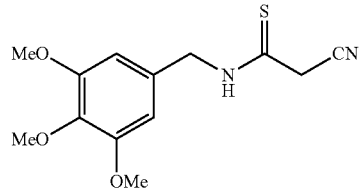 [SMILES: COc1cc(CNC(=S)CC#N)cc(OC)c1OC]

The amide produced in step (a) (1 equiv) and Lawesson's reagent (0.55 equiv) were heated in dry toluene (ca. 2 mL/mmol of the compound obtained in step (a)) under reflux for 3 hours (until TLC indicated the disappearance of the amide). The reaction mixture was cooled and evaporated under reduced pressure. The residue was purified by flash chromatography to yield a pale yellow solid in 50-60% yield.

$^1$H NMR (300 MHz, in Acetone-d$_6$): δ 9.20 (bs, 1H), 6.72 (s, 2H), 4.77 (d, J=5.2 Hz, 2H), 4.06 (s, 2H), 3.80 (s, 6H), 3.71 (s, 3H). MS (CI). found (m/z) 281.51. calculated for C$_{13}$H$_{17}$N$_2$O$_3$S (MH$^+$) 281.34.

C. General Procedure for the Synthesis of Intermediate Compounds Denoted (i) Wherein X$^1$=F, (ii) Wherein X$^1$=Cl, (iii) Wherein X$^1$=Br, (Iv) Wherein X$^1$=I, and (v) Wherein X$^1$=CF$_3$:

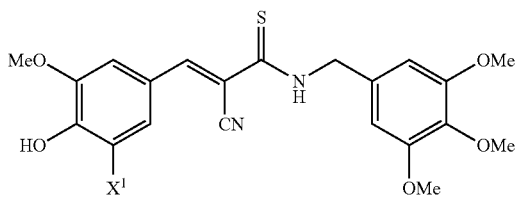
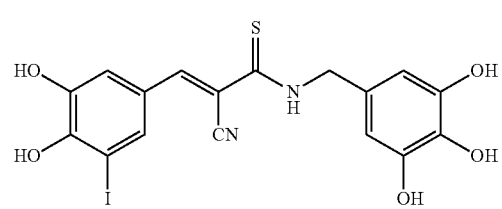 [SMILES: N#C/C(=C\c1cc(O)c(O)c(I)c1)C(=S)NCc1cc(O)c(O)c(O)c1]

A catalytic amount of β-alanine (0.2 equiv) was added to a solution of β-cyanothioamide (1 equiv) and an aldehyde ((1.2 equiv), commercially available except for 3,4-dimethoxy-5-(trifluoromethyl)benzaldehyde which was prepared according to Backstrom et al., *J. Med. Chem.* (1989), 32:841-846) in ethanol (ca. 20 mL/mmol of the compound obtained in step (b)). The solution was heated to 60° C. for 0.5 hour to overnight. The product was precipitated, collected by filtration, washed with $H_2O$, EtOH, and ether and then dried under reduced pressure to yield a pure yellow solid in 70% to quantitative yield.

For Compound (i):

$^1$H NMR (400 MHz, in Acetone-$d_6$): δ 9.60 (bs, 1H), 8.24 (s, 1H), 7.55 (m, 3H), 6.81 (s, 1H), 4.98 (s, 2H), 3.96 (s, 3H), 3.83 (s, 6H), 3.73 (s, 3H).

For Compound (ii):

$^1$H NMR (400 MHz, in $CDCl_3$): δ 8.69 (s, 1H), 7.99 (bt, 1H), 7.58 (d, J=2.0 Hz, 1H), 7.55 (d, J=2.0 Hz, 1H), 6.60 (s, 1H), 4.92 (d, J=5.2 Hz, 2H), 3.96 (s, 3H), 3.87 (s, 6H), 3.84 (s, 3H).

For Compound (iii):

$^1$H NMR (300 MHz, in Acetone-$d_6$): δ 9.62 (bt, 1H), 8.21 (s, 1H), 7.81 (s, 1H), 7.76 (s, 1H), 6.79 (s, 2H), 4.96 (m, 2H), 3.94 (s, 3H), 3.81 (s, 6H), 3.71 (s, 3H). MS (CI). found (m/z) 494.73. calculated for $C_{21}H_{22}BrN_2O_5S$ (MO 494.37.

For Compound (iv):

$^1$H NMR (400 MHz, in $CDCl_3$): δ 8.66 (s, 1H), 7.99 (bt, 1H), 7.86 (d, J=2.0 Hz, 1H), 7.72 (d, J=2.0 Hz, 1H), 6.60 (s, 2H), 4.93 (d, J=5.0 Hz, 2H), 3.97 (s, 3H), 3.88 (s, 6H), 3.86 (s, 3H). MS (CI). found (m/z) 540.67. calculated for $C_{21}H_{21}IN_2O_5S$ (M$^+$) 540.37.

For Compound (v):

$^1$H NMR (200 MHz, in $CDCl_3$): 8.75 (s, 1H), δ 8.22 (bt, 1H), 7.91 (d, J=2.0 Hz, 1H), 7.69 (d, J=2.0 Hz, 1H), 6.61 (s, 2H), 4.94 (d, J=5.0 Hz, 2H), 4.03 (s, 3H), 3.88 (s, 6H), 3.86 (s, 3H).

D. General Procedure for the Synthesis of Compounds of Formula (B) Wherein A=CN:

Boron tribromide (1.5 equiv excess for each hydroxyl group) was added to a cold solution of the protected product in anhydrous $CH_2Cl_2$ (ca. 20 mL/mmol of compounds of step (c)). The reaction mixture was allowed to warm to room temperature and stirred for 2-4 hours (until HPLC indicated the formation of the deprotected compound). The solution was cooled and then treated with dilute hydrochloric acid. The solution was extracted three times with ethyl acetate, the organic layer was dried over $Na_2SO_4$, filtered and the solvent was evaporated. The crude compound was recrystallized from water/ethanol to give yellow solid in 60-70% yield. This procedure can be used to prepare the precursor of compound 2, which is represented by the structure:

$^1$H NMR (200 MHz, in Acetone-$d_6$): δ 9.42 (bs, 1H), 8.24 (s, 1H), 7.91 (d, J=2.1 Hz, 1H), 7.64 (d, J=2.1 Hz, 1H), 6.47 (s, 2H), 4.79 (d, J=5.5 Hz, 2H). MS (ESI). found (m/z) 484.80. calculated for $C_{17}H_{13}IN_2O_5S$ (M$^+$) 484.96. Anal. ($C_{17}H_{13}INO_5S$) C, H, N, I, S Other compounds of formula (B) can be prepared by similar methods.

II. General Procedure for the Synthesis of Precursors of Formula (B) Wherein A=H:

A. General Procedure for the Synthesis of the Following Intermediate Compounds Denoted (vi) Wherein $X^1$=Br, (vii) Wherein $X^1$=I, and (viii) Wherein $X^1$=$CF_3$.

Compounds wherein $X^1$=H or compounds having additional substituents on the phenyl ring can be made in a similar manner.

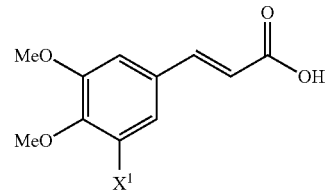

A catalytic amount of piperidine (0.2 equiv) was added to a solution of aldehyde ((1 equiv) commercially available except for 3,4-dimethoxy-5-(trifluoromethyl)benzaldehyde which was prepared according to Backstrom et al., J. Med. Chem. (1989), 32:841-846) and malonic acid (1.5 equiv) in pyridine. The reaction mixture was heated to 120° C. for 6 h. The solution was cooled to room temperature and concentrated HCl was added dropwise to pH<3. The white solid was collected by filtration, washed with water and dried under reduced pressure.

For Compound (vi):

$^1$H NMR (300 MHz, in $CDCl_3$): δ 7.65 (d, J=15.9 Hz), 7.35 (d, J=2.1 Hz, 1H), 7.01 (d, J=2.1 Hz, 1H), 6.35 (d, J=15.9 Hz, 1H), 3.90 (s, 3H), 3.88 (s, 3H).

For Compound (vii):

$^1$H NMR (400 MHz, in $CDCl_3$): δ 7.64 (d, J=2.0 Hz, 1H), 7.56 (d, J=2.0 Hz), 7.04 (d, J=2.0 Hz, 1H), 6.35 (d, J=16.0 Hz, 1H), 3.92 (s, 3H), 3.88 (s, 3H).

For Compound (viii):

$^1$H NMR (400 MHz, in $CDCl_3$): δ 7.63 (d, J=16 Hz), 7.61 (s, 1H), 7.43 (s, 1H), 6.50 (d, J=16 Hz, 1H), 3.90 (s, 3H), 3.88 (s, 3H).

B. General Procedure for the Synthesis of the Following Intermediate Compounds Denoted (ix) Wherein $X^1$=Br, (x) Wherein $X^1$=I, and (xi) Wherein $X^1$=$CF_3$:

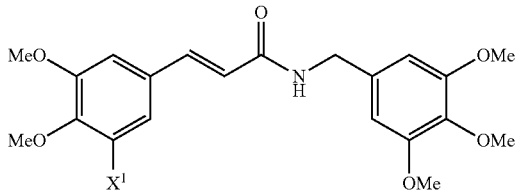

The solution of compounds (vi-viii, 1 equiv) in oxalyl chloride (4 equiv) was stirred for 1-2 hours at room temperature. The excess of oxalyl chloride was distilled off and the mixture was evaporated to dryness. The residue was dissolved in $CH_2Cl_2$ and added drop wise to a solution of an amine (0.85 equiv) and $Et_3N$ (4 equiv) in $CH_2Cl_2$. the reaction mixture was stirred at room temperature for 0.5-1 hour (until TLC indicated the disappearance of the amine). The solvent was evaporated under reduced pressure and the residual oil was purified by flash chromatography.

For Compound (ix):
$^1$H NMR (300 MHz, in $CDCl_3$): δ 7.52 (d, J=15.8 Hz, 1H), 7.29 (s, 1H), 6.92 (s, 1H), 6.50 (s, 2H), 6.37 (d, J=15.8 Hz, 1H), 6.23 (bt, 1H), 4.46 (d, J=5.7 Hz, 2H), 3.81-3.85 (s, 15H). MS (ESI). found (m/z) 467.87. calculated for $C_{21}H_{25}BrNO_6$ (MH$^+$) 466.32.

For Compound (x):
$^1$H NMR (400 MHz, in $CDCl_3$): δ 7.51 (d, J=2.0 Hz, 1H), 7.50 (d, J=15.6 Hz), 6.96 (d, J=2.0 Hz, 1H), 6.51 (s, 2H), 6.35 (d, J=15.6 Hz, 1H), 6.10 (bt, J=5.2 Hz, 1H), 4.47 (d, J=5.2 Hz, 2H), 3.85 (s, 3H), 3.84 (s, 3H) 3.82 (s, 6H), 3.81 (s, 3H).

For Compound (xi):
$^1$H NMR (300 MHz, in $CDCl_3$): δ 7.52 (d, J=15.8 Hz, 1H), 7.29 (s, 1H), 6.92 (s, 1H), 6.50 (s, 2H), 6.37 (d, J=15.8 Hz, 1H), 6.23 (bt, 1H), 4.46 (d, J=5.7 Hz, 2H), 3.81-3.85 (s, 15H). MS (ESI). found (m/z) 467.87. calculated for $C_{21}H_{25}BrNO_6$ (MH$^+$) 466.32.

C. General Procedure for the Synthesis of the Following Compounds Denoted (xii) Wherein $X^1$=Br, (xiii) Wherein $X^1$=I, and (xiv) Wherein $X^1$=$CF_3$:

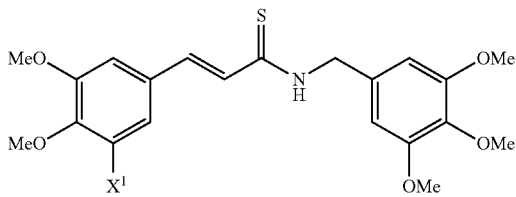

An amide (1 equiv) and Lawesson's reagent (0.55 equiv) were refluxed in toluene for 3 hours (until TLC indicated the disappearance of the amide). The reaction mixture was cooled and evaporated under reduced pressure. The residue was purified by flash chromatography to yield a pale yellow solid in 50-60% yield.

For Compound xii:
$^1$H NMR (300 MHz, in $CDCl_3$): δ 7.75 (d, J=15.3 Hz, 1H), 7.41 (d, J=2.1 Hz, 1H), 7.29 (d, J=2.1 Hz, 1H), 7.16 (d, J=15.3 Hz, 1H), 6.76 (s, 2H), 4.90 (m, 2H), 3.94 (s, 3H), 3.83 (s, 3H), 3.77 (s, 6H), 3.70 (s, 3H). MS (ESI). found (m/z) 483.87. calculated for $C_{21}H_{25}BrNO_5S$ (MH$^+$) 483.38.

For Compound (xiii):
$^1$H NMR (400 MHz, in $CDCl_3$): δ 7.71 (d, J=15.2 Hz, 1H), 7.6 (bt, 1H), 7.56 (d, J=1.8 Hz, 1H), 7.01 (d, J=1.8 Hz, 1H), 6.78 (d, J=15.2 Hz, 1H), 6.55 (s, 2H), 4.86 (d, J=5.0 Hz, 2H), 3.86 (s, 3H), 3.84 (s, 3H), 3.83 (s, 6H), 3.82 (s, 3H).

For Compound (xiv):
$^1$H NMR (300 MHz, in $CDCl_3$): δ 7.75 (d, J=15.3 Hz, 1H), 7.41 (d, J=2.1 Hz, 1H), 7.29 (d, J=2.1 Hz, 1H), 7.16 (d, J=15.3 Hz, 1H), 6.76 (s, 2H), 4.90 (m, 2H), 3.94 (s, 3H), 3.83 (s, 3H), 3.77 (s, 6H), 3.70 (s, 3H). MS (ESI). found (m/z) 483.87. calculated for $C_{21}H_{25}BrNO_5S$ (MH$^+$) 483.38.

D. General Procedure for the Synthesis Compounds of Formula (B) Wherein A=H:
Compounds of formula (B) wherein A=H may be prepared in the same manner as set forth in step (I)(D) described above for the corresponding compounds of formula (B) wherein A=CN. This procedure can be used to prepare the precursors of compounds 3-9, which are represented by the structures

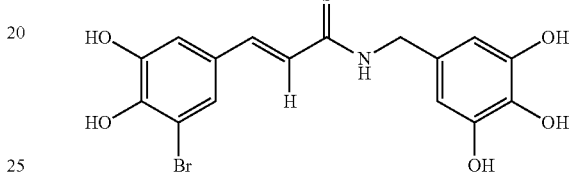

Precursor of Compounds 3 and 6

$^1$H NMR (400 MHz, in Acetone-$d_6$): δ 9.16 (bs, 1H), 7.69 (d, J=15.4 Hz, 1H), 7.31 (d, J=1.9 Hz, 1H), 7.09 (d, J=1.9 Hz, 1H), 7.06 (d, J=15.4 Hz, 1H), 6.44 (s, 2H), 4.76 (d, J=5.7 Hz, 2H). MS (ESI). found (m/z) 411.93. calculated for $C_{16}H_{15}BrNO_5S$ (MH$^+$) 411.97. Anal. ($C_{16}H_{14}BrNO_5S$) C, H, N, Br, S

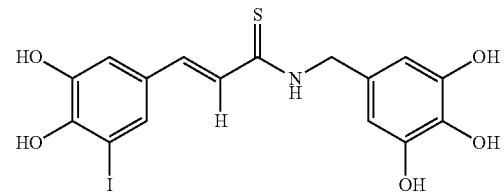 [SMILES: Oc1cc(CNC(=S)/C=C/c2cc(O)c(O)c(I)c2)cc(O)c1O]

Precursor of Compound 4

$^1$H NMR (400 MHz, in Acetone-$d_6$): δ 9.2 (bs, 1H), 7.67 (d, J=15.2 Hz, 1H), 7.51 (d, J=2.0 Hz, 1H), 7.12 (d, J=2.0 Hz, 1H), 7.02 (d, J=15.2 Hz, 1H), 6.44 (s, 2H), 4.76 (d, J=5.2 Hz, 2H). MS (ESI). found (m/z) 460.13. calculated for $C_{16}H_{15}INO_5S$ (MO 460.26. Anal. ($C_{16}H_{14}INO_5S$) C, H, N, I, S

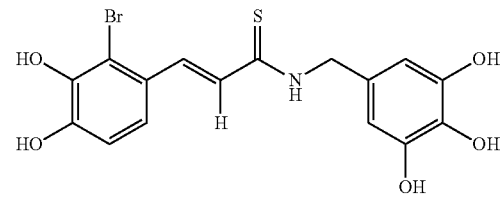 [SMILES: Oc1cc(CNC(=S)/C=C/c2ccc(O)c(O)c2Br)cc(O)c1O]

Precursor of Compound 5

$^1$H NMR (300 MHz, CDCl$_3$): δ 4.77 (d, 2H, J=5.2 Hz, CH$_2$N), 6.43 (s, 2H, aromatic), 6.86 (d, 1H, J=8.4 Hz, aromatic), 7.01 (d, 1H, J=15.2 Hz, alkene), 7.16 (d, 1H, J=8.4 Hz, aromatic), 8.27 (d, 1H, J=15.2 Hz, alkene), 8.99 (br.s., 1H, NH). Anal. (C$_{16}$H$_{14}$BrNO$_5$S) C, H, N, Br, S

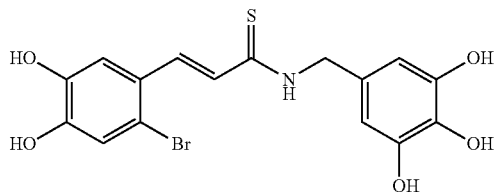 [SMILES: Oc1cc(Br)c(/C=C/C(=S)NCc2cc(O)c(O)c(O)c2)cc1O]

Precursor of Compound 7

$^1$H NMR (400 MHz, CDCl$_3$): δ 8.20 (d, J=15.2 Hz, 1H, Ar—C$\underline{H}$=CH), 7.23 (s, 1H, aromatic CH), 7.12 (s, 1H, aromatic CH), 6.99 (d, J=15.2 Hz, 1H, 1H, Ar—CH=C$\underline{H}$), 6.46 (s, 2H, aromatic CH), 4.79 (d, J=5.6 Hz, 2H, CH$_2$N).

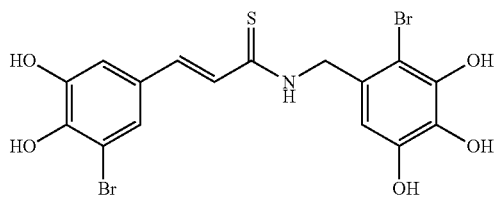 [SMILES: Oc1cc(/C=C/C(=S)NCc2cc(O)c(O)c(O)c2Br)cc(Br)c1O]

Precursor of Compound 8

δ 9.10 (bt, 1H), 7.70 (d, J=15.2 Hz, 1H), 7.32 (d, J=2 Hz, 1H), 7.12 (d, J=2 Hz, 1H), 7.08 (d, J=15.2 Hz, 1H), 6.60 (s, 1H), 4.91 (d, J=4.8 Hz, 2H).

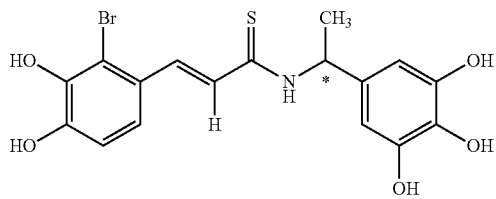 [SMILES: CC(NC(=S)/C=C/c1ccc(O)c(O)c1Br)c1cc(O)c(O)c(O)c1]

Precursor of Compound 9

$^1$H NMR (400 MHz, in Acetone-d$_6$): δ 1.54 (d, 3H, J=5.2 Hz, CH$_3$), 5.84 (q, 1H, J=7 Hz, CH), 6.49 (s, 2H, aromatic), 6.89 (d, 1H, J=8.8 Hz, aromatic), 7.0 (d, 1H, J=15.2 Hz, alkene), 7.17 (d, 1H, J=8.4 Hz, aromatic), 8.21 (d, 1H, J=12.8 Hz, alkene), 9.18 (d., 1H, NH, J=8).

It is noted that all enantiomers and diastereomers of the compounds of the present invention and their precursors are included within the scope of the invention. For example, the compound of formula 9 is chiral. The present invention contemplates the use of the R and S enantiomers, mixtures thereof in any ratio, as well as the racemic mixtures.

Other compounds of formula (B) can be prepared by similar methods.

Examples 2-7

Biological Activity

Reagents and Antibodies

All chemicals used for chemical synthesis, as well as IGF1 and methylene blue were purchased from Sigma. WST-1 reagent was from Roche. Anti-phospho(Y896)IRS1 antibody was obtained from Oncogene Research Products, Germany; anti-IRS1 was obtained from Upstate Biotechnology, Inc.; anti-IRS2 was obtained from Abcam; anti-Akt1/2(PKB), anti-ERK2, and anti-IGF-IRβ antibodies were obtained from Santa Cruz Biotechnology. Anti-phospho(T308)Akt (pPKB), anti-phospho(Ser636/Ser639)IRS1 and anti-phospho (Y1131)IGF-1R/(Y1146)IR (pIGF-IR) antibodies were obtained from Cell Signaling Technology. Dulbecco's modified Eagle's medium (DMEM) and fetal calf serum (FCS) were obtained from Biological Industries, Bet-Haemek, Israel. DMSO was obtained from BDH.

Example 2

Inhibition of Cell Proliferation

Human ovary cancer A2780 cells lines were seeded at a density of 5000 cells/well, human melanoma A375 cells were plated at a density of 2,500 cells/well, human colon carcinoma HCT15 cells were plated at a density of 3,000 cells/well, human prostate carcinoma PC3 cells were plated at a density of 1,500 cells/well, human breast carcinoma MCF7 cells were plated at a density of 5,000 cells/well, human breast carcinoma MDA MB 468 cells were plated at a density of 6,000 cells/well, human myeloma U266, RPMI8226 and CAG cells were plated at a density of 10,000 cells/well. All cells were plated in 96-well plates in 90 μl growth medium containing 10% FCS, 100 units/ml penicillin and 100 μg/ml streptomycin. Compound 3 was added a day later in 10 μA of 1% DMSO in DDW to obtain final concentrations of 0, 0.1, 0.3, 1, 3, and 10 μM. The final concentration of DMSO (0.1% DMSO) was kept constant in all samples. Following exposure of the cells to compound 3 for 72 hours at 37° C., adhered cells were fixed in 0.5% gluteraldehyde in medium for 10 min, washed three times with DDW, once with 0.1M sodium borate buffer pH 8.5 and stained with 1% methylene blue dissolved in 0.1M borate buffer solution for 60 min. Excess dye was washed out and cell-bound dye was eluted with 200 μl/well of 0.1M HCl. The optical density values were read at 630 nm in ELISA plate reader. Non-adhered cells were exposed to WST-1 reagent for 5 hours following 72 hours treatment with the inhibitors, and optical density values were read at 630 nm in ELISA plate reader. The data was analyzed in Microsoft Excel, using the vehicle control as 100% proliferation. The assays were performed in triplicates. The values of IC$_{50}$ were derived from the dose-dependent growth curves obtained.

As can be seen in Table 1, compound 3 was found to inhibit several cancerous cell lines of various cancer types. Hence, the compounds of the present invention are potent as anti-cancerous agents.

TABLE 1

| Cancer Type | Cell line | IC$_{50}$(μM) |
| --- | --- | --- |
| Melanoma | A375 | 1 |
| Ovary | A2780 | 0.3 |
| Prostate | PC3 | 2 |
| Colon | HCT15 | 1 |
| Multiple Myeloma | U266 | 0.7 |
| Multiple Myeloma | RPMI8226 | 2 |
| Multiple Myeloma | CAG | 1.2 |
| Breast Cancer | MDA-468 | 3.8 |

Example 3

Inhibition of IGF-1R Related Signaling in Cancer Cells

Tyrosine autophosphorylation of the β-subunit of IGF-1R as well as downstream signaling induced by IGF-1R were assayed in human breast cancer MCF7 cells and in melanoma A375 cells. Cells were seeded in 6-well plates (250,000 A375 cells/well and 300,000 MCF7 cells/well) and 24 hours later medium was replaced by serum-free medium (RPMI supplemented with 100 units/ml penicillin and 100 μg/ml streptomycin). MCF7 cells were exposed for 48 hr to compound 3 at 10 μM concentration, and then stimulated for 5 minutes with 50 ng/ml IGF-1, washed twice with PBS and lysed by boiling sample buffer (10% glycerol, 50 mM Tris-HCl, pH 6.8, 3% SDS, and 5% (3-mercaptoethanol). Equal amounts of protein per lane were separated by 8% SDS-PAGE and transferred to a nitrocellulose membrane (Sartorius AG). Phosphorylated proteins were immunoblotted with anti-phosphoIGF-1R (pIGF-1R), anti-phosphotyrosine-IRS1 (pY-IRS I) and anti-phospho(T308)Akt (pPKB) antibodies. Detection was performed with horseradish peroxidase-conjugated secondary antibody using the ECL system. Blots were then stripped of antibodies, blocked with TBST with 5% low fat milk and re-probed with antibodies detecting both the phosphorylated and the non-phosphorylated corresponding proteins e.g. IGF-1Rβ, IRS1 and PKB.

In addition, lysates of human melanoma A375 cells were prepared from cells exposed to compound 3 at 1 and 3 μM concentrations in serum-free medium. Stimulation, lysate preparation and western blot were performed as described above. In this experiment the phosphorylated form of IRS1 on Serine-636/639 and the levels of IRS2 were detected as well.

Figure 5:
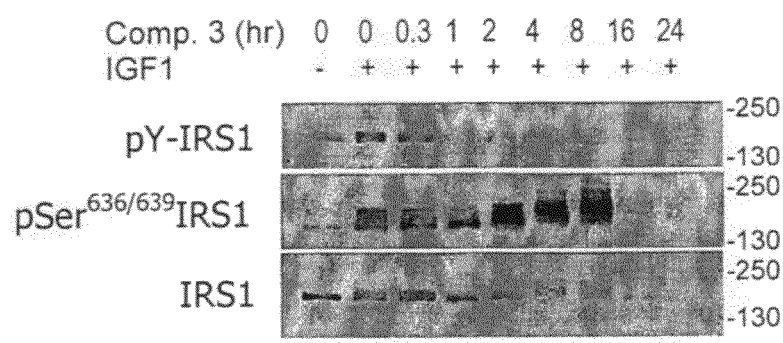
FIG. 5 Shows the time course of the effect of compound 3 on IRS1 in breast cancer MCF7 cells.

The time course of the effects of compound 3 on IRS1 phosphorylation and levels was investigated by the same procedure, following treatment of breast cancer MCF7 cells with 10 μM concentration of compound 3 for various time periods indicated in FIG. 5, stimulation with IGF1 and immunoblotting.

Figure 3:
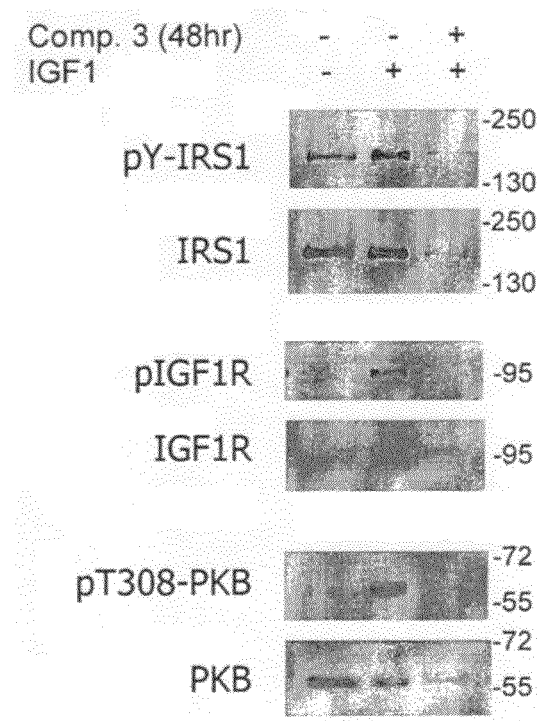
FIG. 3 Shows the effect of compound 3 on IGF1-induced signaling in breast cancer MCF7 cells, 48 hr following treatment.
Figure 4:
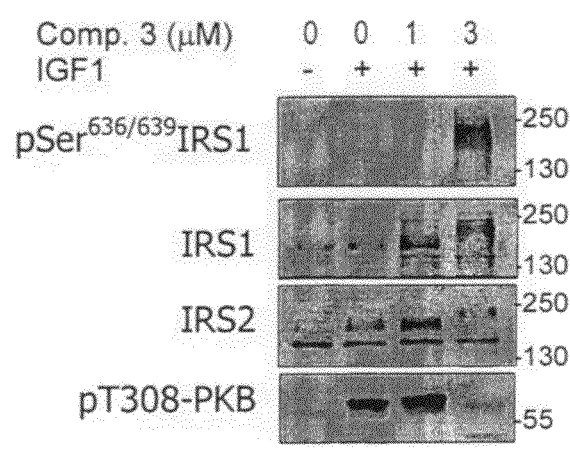
FIG. 4 Shows the induction of IRS1 and IRS2 serine phosphorylation and inhibition of IGF1-induced PKB/Akt activation in melanoma A375 cells treated 4 hr with compound 3.

Compound 3 of the present invention was tested for its effect on several components of the IGF-1R signaling axis, including IGF-1R, IRS1 and PKB. As can be seen in FIG. 3, compound 3 significantly inhibited the IGF1-induced autophosphorylation of IGF-1R and the IGF1-induced activation of the downstream signaling component PKB, a central anti-apoptotic signaling protein. In addition, compound 3 was found to induce a significant decrease in the levels of IRS1, a direct substrate of IGF-1R, thereby blocking its signal for a very long time. The inhibitory effect of compound 3 is long-lasting (more than 48 hr) as demonstrated in FIG. 3. FIG. 5 demonstrates that the elimination of IRS1 induced by compound 3 is subsequent to IRS1 serine phosphorylation. The Ser-phosphorylation of IRS1 and IRS2 is demonstrated by specific antibodies to phosphor-Serines636/639-IRS1 and by the up-shift of these proteins in SDS-PAGE (FIGS. 4 & 5). Without being bound by any theory or mechanism of action, Ser-phosphorylation of IRS1 induces decoupling of IRS1 and IGF-1R and, therefore, inhibits IGF-1R signaling. This phosphorylation and the decrease in IRS1 levels result in a long-term inhibition of IGF-1R signal transduction.

Example 4

Inhibition of Cell Proliferation

Cell proliferation assay was performed as described in Example 2. The following cell line were plated in 96-well plates in 90 μl growth medium containing 10% FCS, 100 units/ml penicillin and 100 μg/ml streptomycin: human ovary cancer A2780 cells (4500 cells/well), human melanoma A375 (1500 cells/well) and YUMAC (2500 cells/well) cells, human colon carcinoma HCT15 (3000 cells/well) and HCT116 (2000 cells/well) cells, human prostate carcinoma PC3 (3000 cells/well), PC3MM2 (3500 cells/well) and DU145 (300 cells/well) cells, human hepatocarcinoma HepG2 (3000 cells/well), human Ewing sarcoma SK-ES-1 (4,500 cells/well), human glioblastoma U138MG (2,000 cells/well), human breast cancer T47D (4000 cells/well) and MDA-MB-468 (6000 cells/well) cells, human small cell lung carcinoma NCI-H1975 (5000 cells/well) cells, human osteosarcoma Saos-2 (5000 cells/well) cells, human pancreatic cancer ASPC (2500 cells/well) cells, human bladder carcinoma T24P (1000 cells/well) cells, human gastric cancer NCI-N87 (5000 cells/well) cells, human lymphoma KARPAS (5,000 cells/well) cells, human leukemia K562 (5,000 cells/well) cells and human multiple myeloma MM1S (10,000 cells/well), U266 (10,000 cells/well) and CAG (5,000 cells/well). Compounds 2-5 and 7-8 were added a day later in 10 μl of 0.7% 2-hydroxypropyl-β-cyclodextrin to obtain final concentrations of 0, 0.1, 0.3, 1, 3 and 10 μM.

Compounds 2-5 and 7-8 of the present invention were tested for their inhibitory potential in cell proliferation assay. Human ovary cancer A2780 cells, human melanoma A375 and YUMAC cells, human colon carcinoma HCT15 and HCT116 cells, human prostate carcinoma PC3, PC3MM2 and DU145 cells, human hepatocarcinoma HepG2 cells, human Ewing sarcoma SK-ES-1 cells, human glioblastoma U138MG cells, human breast cancer T47D and MDA-MB-468 cells, human small cell lung carcinoma NCI-H1975 cells, human osteosarcoma Saos-2 cells, human pancreatic cancer ASPC cells, human bladder cancer T24P cells, human gastric cancer cells, human lymphoma KARPAS cells, human leukemia K562 cells, and human multiple myeloma MM1S, CAG and U266 cells, were exposed to increasing concentrations of compounds 2-5 and 7-8. IC$_{50}$ values were determined from the curves of the optical density against compound concentration. The assay was performed in triplicates. As can be seen in Table 2, compounds 2-5 and 7-8 were found to inhibit several cancerous cell lines of various cancer types. Hence, the compounds of the present invention are potent anti-cancer agents.

TABLE 2

| Cell line | Cancer | IC$_{50}$ (μM) Compound # | | | | | |
|---|---|---|---|---|---|---|---|
| | | 2 | 3 | 4 | 5 | 7 | 8 |
| A2780 | Ovary Cancer | 0.6 | 0.4 | 0.3 | 0.4 | | |
| A375 | Melanoma | | 0.5 | | 0.4 | | |
| YUMAC | | | 0.3 | 0.5 | 0.2 | 0.5 | 0.5 |
| HCT116 | Colon Cancer | | 0.5 | 0.7 | 0.4 | 1.4 | 0.8 |
| HCT15 | | | 0.7 | | 0.9 | | |
| PC3 | Prostate Cancer | | 0.7 | | | | |
| PC3MM2 | | | 2.3 | 0.9 | 1.8 | | |
| DU145 | | | 2.3 | 2.0 | 2.7 | 2.3 | |
| HepG2 | Hepatocarcinoma | 2.8 | 0.9 | 2.7 | 1.6 | | |
| SK-ES-1 | Ewing Sarcoma | | 0.3 | 0.2 | 0.6 | 0.2 | |
| U138MG | Glioblastoma | | 0.3 | 0.3 | 0.3 | 0.8 | |
| T47D | Breast cancer | | 1.5 | 0.7 | 1.8 | | |
| MDA-MB-468 | | 1.2 | 4.7 | 2.2 | 2.9 | | |
| NCI-H1975 | SCLC | | 1.0 | 1.1 | 0.8 | 2.6 | |
| Saos-2 | Osteosarcoma | | 3.1 | 2.0 | 2.8 | 2.7 | |
| ASPC | Pancreatic Cancer | | 13.1 | 18.5 | 8.2 | 13.3 | 17.7 |
| T24P | Bladder | | 6.0 | 3.2 | 6.5 | 4.5 | |
| NCI-N87 | Gastric | | 4.5 | 4.8 | 4.0 | 8.4 | |
| KARPAS | Lymphoma | | 0.5 | 1.5 | 0.9 | 1.8 | |
| K562 | Leukemia | | 0.5 | 0.9 | 0.5 | 1.8 | 0.8 |
| CAG | Multiple | | 0.9 | 3.0 | 0.7 | 4.9 | |
| MM1S | Myeloma | 2.0 | 0.5 | 0.7 | 0.6 | 0.2 | 0.5 |
| U266 | | | 0.7 | | | | |

Example 5

Inhibition of IGF-1R Related Signaling and Apoptosis in Cancer Cells

The effect of compound 5 on IRS1 & IRS2 levels and its effect on IGF1-induced Akt/PKB activation and apoptosis in melanoma A375 cells were tested. Cells were seeded in 6-well plates (150,000 A375 cells/well) and 24 hours later medium was replaced by serum-free medium (RPMI supplemented with 100 units/ml penicillin and 100 μg/ml streptomycin), exposed to compound 5 at 3 μM concentration for 48 hr, and then stimulated for 5 minutes with 50 ng/ml IGF-1, washed twice with PBS and lysed by boiling sample buffer (10% glycerol, 50 mM Tris-HCl, pH 6.8, 3% SDS, and 5% β-mercaptoethanol). Equal amounts of protein per lane were separated by 8% SDS-PAGE and transferred to a nitrocellulose membrane (Sartorius AG). To detect the inhibition of the Akt/PKB activation, phosphorylated proteins were immunoblotted with anti-phospho(T308)Akt (pT308-PKB) and anti-phospho-Tuberin/TSC2 (pTuberin) antibodies. To visualize cell death induced by compound 5, the intact and the cleaved PARP were immunoblotted with anti-PARP antibody. The changes in the levels of IRS1 and IRS2 were detected with specific antibodies. Detection was performed with horseradish peroxidase-conjugated secondary antibody using the ECL system. Blots were then stripped of antibodies, blocked with TBST with 5% low fat milk and re-probed with antibodies detecting both the phosphorylated and the non-phosphorylated Akt/PKB.

In addition, lysates of human melanoma A375 cells were prepared from cells exposed to compound 2, 3, 4 and 5 at 3 μM concentrations in serum-free medium for 48 hr. Lysate preparation and western blot were performed as described above. IRS1 levels and PARP cleavage were visualized.

Figure 6A:
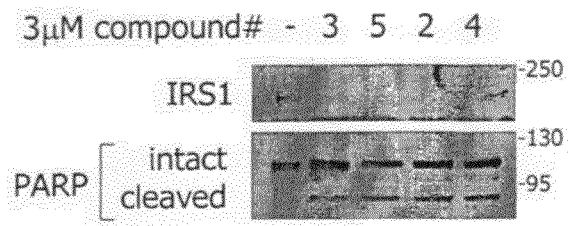
FIG. 6 Shows the effect of compounds 2-5 on IRS1 & IRS2 elimination in human melanoma A375 cells (FIG. 6A), and the subsequent effect of compound 5 on IGF1-induced PKB/Akt activation (FIG. 6B).
Figure 6B:
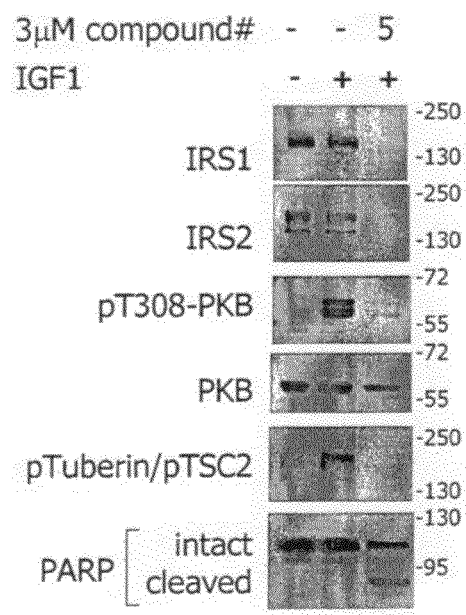

Compounds 2-5 of the present invention were tested for their effect on IRS1 levels and cell apoptosis following 48 hr treatment with 3 μM concentrations. As can be seen in FIG. 6A these compounds induced a dramatic decrease in IRS1 levels and further induced cell death, as demonstrated by the massive cleavage of PARP. Compound 5 induced a decrease in IRS1 & IRS2 levels and blocked the IGF1-induced activation of the central anti-apoptotic Akt/PKB pathway. The activation of Akt/PKB pathway was demonstrated by the increase in Akt/PKB phosphorylation on Thr308 and by the increase in the phosphorylation on Akt/PKB's direct substrate Tuberin/TSC2. FIG. 6B shows that treating human melanoma A375 cells for 48 hr with 3 μM of compound 5 induced a decrease in IRS1 and IRS2 levels, blocked the IGF1-induced activation of the Akt/PKB pathway and induced cell death (PARP cleavage).

Figure 6C:
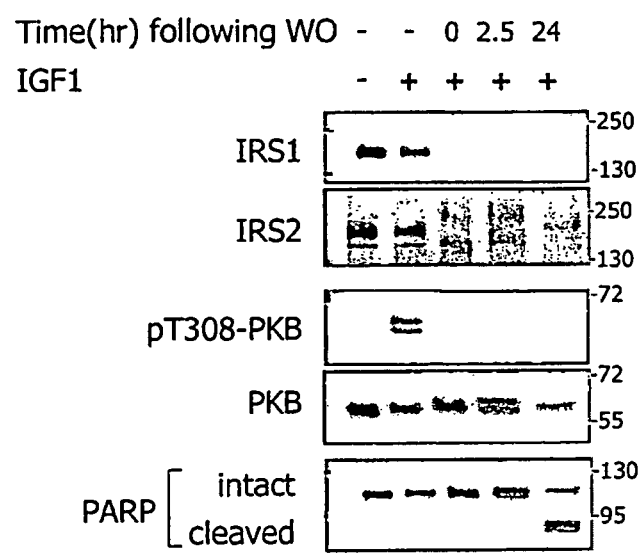

In order to test whether a short exposure to compound 5 would suffice to trigger a long-term inhibition of IGF1-induced signaling and cancer cell apoptosis, serum-starved human melanoma A375 cells were treated with compound 5 at 5 μM concentration for 4 hr. Cells were then washed twice with medium and incubated in a serum-free medium for 0, 2.5 and 24 hr, stimulated with 50 ng/ml IGF1 for 5 min and lysed. As can be seen in FIG. 6C, the effect of compound 5 on IRS1 & IRS2 elimination was not recovered even 24 hr after compound 5 was washed out, the levels of IRS1 & IRS2 remained low and IGF1-induced activation of PKB/Akt, a central anti-apoptotic protein, was blocked. As indicated by PARP cleavage 24 hr following compound 5 washout (WO), 4 hr treatment with compound 5 were enough to trigger a process which leads to cell death.

Example 6

Inhibition of Ovarian Tumor Growth In-Vivo

In order to determine the effect of the compounds of the present invention on the growth and spread of tumors in-vivo, the compounds were administered to nude mice bearing human ovarian cancer. The involvement of IGF-1R/IRS pathway in this indication is known, and IRS1 upregulation in particular has been demonstrated in ovary cancer (Ravikumar et al., *Cancer Res.*, (2007), 67: 9266-9275). A model of peritoneal carcinomatosis formation, involving intraperitoneal administration of human ovary A2780 tumor cells, was used.

Two million human ovarian A2780 cells were injected to the peritoneum of 4-5 weeks old female nude mice. A week later, treatments with compound 3 or vehicle were initiated. Compound 3 was administered IV, daily at a dose of 3 mg/kg or weekly at a dose of 12 mg/kg for the time periods indicated in FIG. 7. The control group was weekly administered (IV) with the vehicle (20% 2-hydroxypropyl-b-cyclodextrin). Each group included 10 mice. Mice were observed at least three times a week, and sacrificed when tumor signs appeared (abdominal distension).

Figure 7:
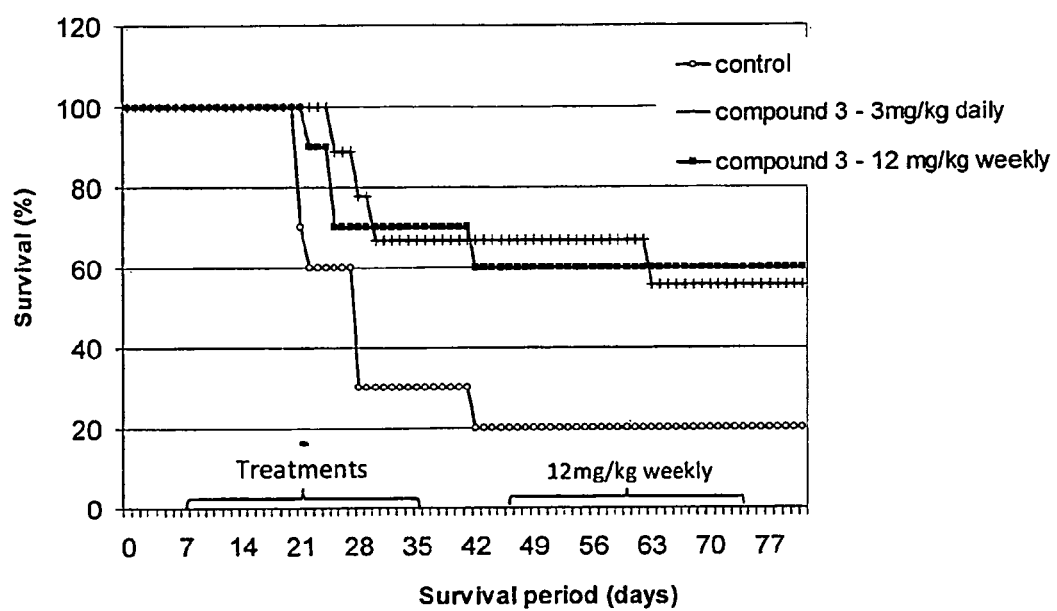
FIG. 7 Shows the effect of IV administration of compound 3 on the survival of nude mice bearing intra peritoneal ovary cancer.

As can be seen in FIG. 7, in a mouse survival model of human ovarian cancer peritoneal tumors, intravenous treatment of the mice with compound 3 resulted in dramatically increased survival, compared to control mice. While in the control group, the median survival time was 28 days, the median survival time of the animals treated with compound 3, either daily or weekly, was over 81 days.

In a subsequent experiment, performed in the same manner, compound 3 (50 mg/kg, daily IV) showed a preferable median survival time as compared to Cisplatin (3 mg/kg, 3 times a week for two weeks, ip), an approved drug for ovary cancer, and compared to Sunitinib (40 mg/kg daily PO), a tyrosine kinase approved for various cancer indications (data not shown).

Example 7

Synergistic Anti-Proliferative Effect of the Combination with Other Agents

Human multiple myeloma MM1S cells were plated at a density of 10,000 cells/well in 96-well plates in 90 μl growth medium containing 10% FCS, 100 units/ml penicillin and 100 μg/ml streptomycin. Velcade® (i.e. bortezomib or PS-341) was obtained from LC Laboratories.

Compounds 3 and 5 were added a day later in 5 μl of 0.7% 2-hydroxypropyl-β-cyclodextrin in DDW to the multiple myeloma cell plates to obtain final concentrations of 0, 0.1 or 0.2 M. Velcade® was added in 5 μl of 1% DMSO to obtain final concentrations of 0, 0.5, 1 and 1.5 nM. Three days later CellTiter Glo reagent (100 μl/well) was added to the medium (1:1), shaked, and following 10 min incubation transferred to 96-well white plates and read in a Luminometer. The data was analyzed in Microsoft Excel, using the vehicle control as 0% cytotoxicity. The assays were performed in triplicates. Cytotoxicity (%) was calculated as follows: [(absorbance of control cells—absorbance of drug-treated cells)/absorbance of control cells]×100.

Figure 8:
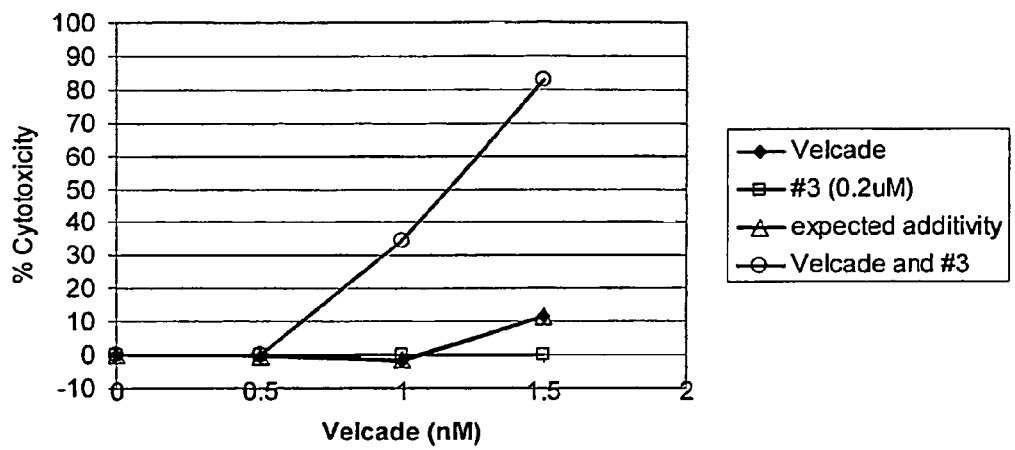
FIG. 8 Demonstrates that treatment with both compound 3 and Velcade has a synergistic cytotoxic effect on multiple myeloma cells.
Figure 9:
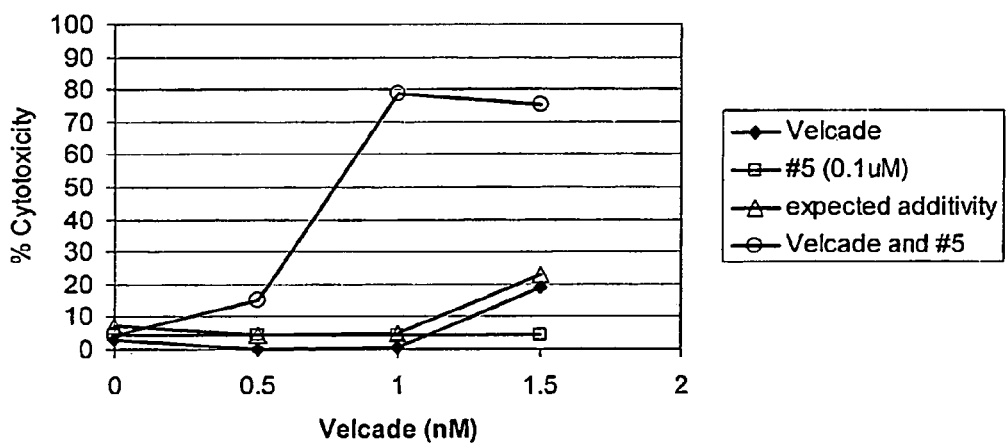
FIG. 9 Demonstrates that treatment with both compound 5 and Velcade has a synergistic cytotoxic effect on multiple myeloma cells.

In FIGS. 8 and 9 the Bliss additivism model (Cardone et al. Science (1998), 282: 1318-1321) was used to calculate the combined effect using the following formula: Ebliss=EA+EB−EA×EB, where EA and EB are the fractional inhibitions obtained by drug A alone and drug B alone at specific concentrations. As can be seen in FIGS. 8 and 9 there is a strong synergistic effect for the combined treatment of Velcade® and compound 3 or 5 in multiple myeloma MM1S cells. In other words, the combined effect of Velcade® and either compound 3 or 5 is significantly higher than the expected additive effect at both 1 and 1.5 nM Velcade®. The synergic effect was calculated in an additional method in which the existence of α/a+β/b<1 was tested (a is the IC50 of drug A in the absence of drug B, α is the IC50 of drug A in the presence of drug B, b is the IC50 of drug B in the absence of drug A, β is the IC50 of drug B in the presence of drug A). The values of α/a+β/b were 0.6 for compound 5 & Velcade®, and 0.7 for compound 3 & Velcade®, approving synergism for the combined therapy in multiple myeloma cells.

Example 8

Anchorage-Independent Growth Assay (Colony Formation in Soft Agar)

Suspensions of separated human metastatic melanoma A375 and glioblastoma U138MG cells are plated in 50 μl growth medium containing 0.3% agar on top of a 100 μl layer of growth medium containing 1% agar in 96-well plates. Growth medium (50 μl) supplemented with the compounds of the present invention at various concentrations is added on top. Six to seven days after plating, colonies are stained with 0.5% MTT for 4 hours, and dye is then extracted by the addition of 100 μl dissolving buffer, containing 5 gr sodium dodecyl sulfate, 8.75 ml DDW, 12.5 ml dimethyl formamide, 0.5 ml acetic acid and 0.07 ml HCl. Following incubation overnight at 37° C., optical density values are read at 570 nm in ELISA plate reader. The data is analyzed in Microsoft Excel, using the vehicle control as 100% proliferation. The assays are performed in triplicates. The values of IC50 are derived from the dose-dependent growth curves obtained.

While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A compound represented by the structure of formula 1:

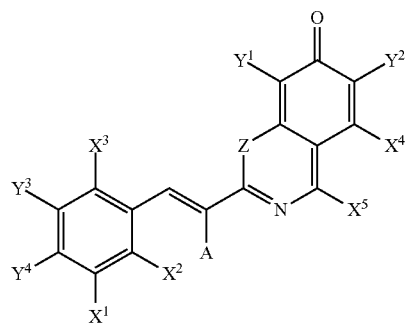

wherein

A is H or CN;

Z is S, SO or $SO_2$;

$X^1$, $X^2$, $X^3$, $X^4$, $X^5$, $Y^1$ and $Y^2$ are each independently selected from H, halogen, alkyl, haloalkyl and $OR^1$; and $Y^3$ and $Y^4$ are each $OR^1$, wherein each $R^1$ is independently H, $C_1$-$C_4$ alkyl, acyl, —$(CH_2CH_2O)_n$ wherein n is an integer of 1 to 20, or a functional group that gives rise to hydroxyl upon hydrolysis, including salts, hydrates, solvates, polymorphs, optical isomers, geometrical isomers, enantiomers, diastereomers, and mixtures thereof.

2. A compound according to claim 1, wherein A is H.

3. A compound according to claim 1, wherein A is CN.

4. A compound according to claim 1, wherein Z is S.

5. A compound according to claim 1, wherein Z is $SO_2$.

6. A compound according to claim 1, wherein at least one of $X^1$, $X^2$, $X^3$, $X^4$, $Y^1$ and $Y^2$ is a halogen; or $X^1$, $X^2$, $X^3$, and $X^4$ are each H or a halogen; or $Y^3$ and $Y^4$ are each OH; or $Y^1$ and $Y^2$ are each OH.

7. A compound according to claim 1, wherein

A is H, Z is S, $Y^3$ and $Y^4$ are each OH, and $X^1$ is a halogen selected from Br and I; or A is CN, Z is S, $Y^3$ and $Y^4$ are each OH, and $X^1$ is a halogen selected from Br and I; or A is H, Z is S, $Y^3$ and $Y^4$ are each OH, and $X^3$ is a halogen selected from Br and I; or A is H, Z is S, $Y^3$ and $Y^4$ are each OH, and $X^2$ is a halogen selected from Br and I; or A is H, Z is S, $Y^3$ and $Y^4$ are each OH, and $X^1$ and $X^4$ are each a halogen selected from Br and I; or A is H, Z is $SO_2$, $Y^3$ and $Y^4$ are each OH, and $X^1$ is a halogen selected from Br and I; or A is H, Z is $SO_2$, $Y^3$ and $Y^4$ are each OH, and at least one of $X^1$, $X^2$, $X^3$, $X^4$, $Y^1$ and $Y^2$ is a halogen.

8. A compound according to claim 1, wherein $X^2$ is H; or $X^5$ is H or alkyl.

9. A compound according to claim 1, selected from the group consisting of:

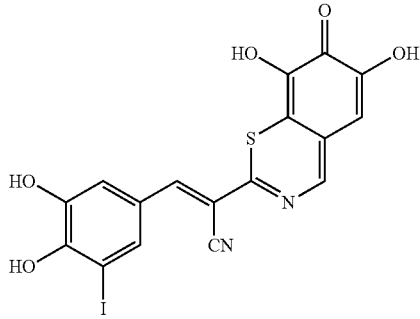
2

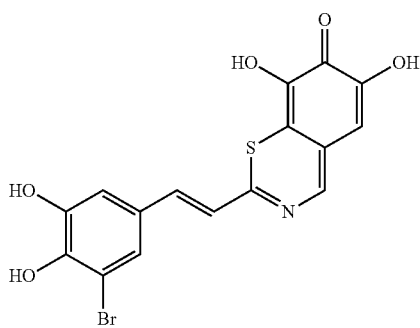
3

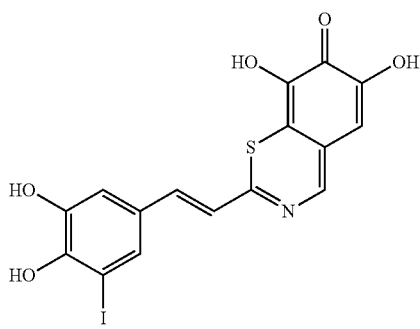
4

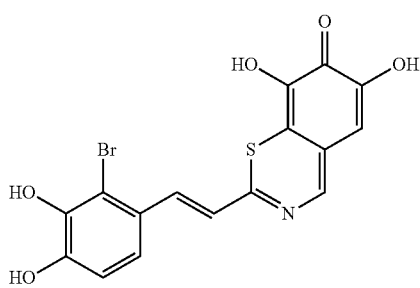
5

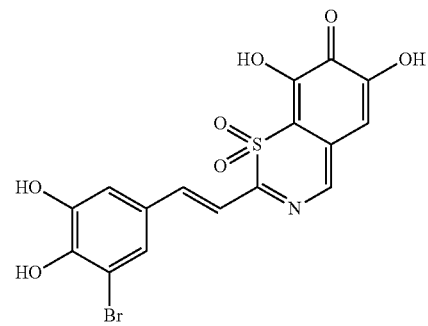
6

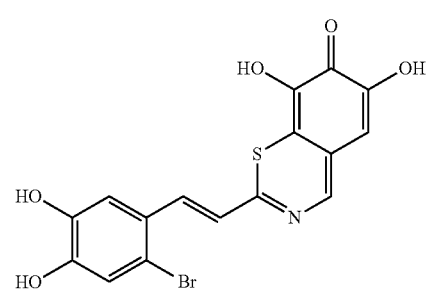
7

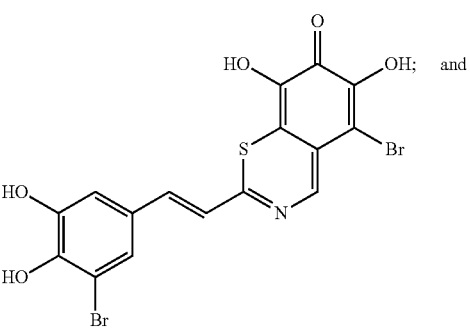
8

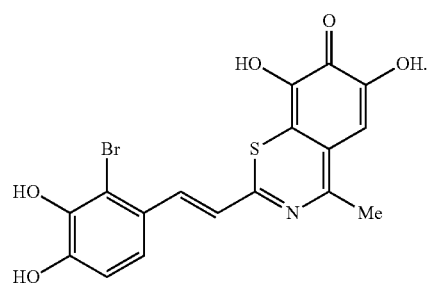
9

10. A pharmaceutical composition comprising a therapeutically effective amount a compound according to claim 1, and a pharmaceutically acceptable carrier or excipient.

11. A pharmaceutical composition comprising a therapeutically effective amount of a compound according to claim 1, in combination with at least one other anti-cancer agent.

12. A method of inhibiting signal transduction mediated by a protein kinase (PK), comprising the step of contacting a cell comprising said PK with a compound according to claim 1; wherein the protein kinase is IGF-1R.

13. The method according to claim 12, wherein the compound of formula (1) directly or indirectly interacts with, affects or inhibits said PK or a protein in said PK-mediated pathway; wherein the protein kinase is IGF-1R.

14. The method according to claim 13, wherein the compound of formula (1) is an inhibitor of an insulin receptor or an insulin-like growth factor-1 receptor (IGF-1R), or wherein the compound of formula (1) directly or indirectly interacts with, affects or inhibits a substrate protein in the IGF-1R mediated pathway.

15. The method according to claim 14, wherein the substrate protein is Insulin Receptor Substrate 1 (IRS1), Insulin Receptor Substrate 2 (IRS2), or a combination thereof, wherein said compound of formula (1) leads to any one or more of (i) dissociation of IRS1 or IRS2 from the cell membrane; (ii) phosphorylation of IRS1 or IRS2; or (iii) degradation of IRS1 or IRS2, in any order.

16. A method for treating an insulin-like growth factor I receptor (IGF-1R), an insulin receptor substrate 1 (IRS1) or an insulin receptor substrate 2 (IRS2) signaling related disorder in a subject, comprising the step of administering to the subject a compound according to claim 1; wherein the disorder is cancer.

17. A method of inhibiting proliferation of a cancer cell selected from the group consisting of melanoma, ovary, prostate, colon, multiple myeloma, and breast cancer cell comprising contacting the cell with a compound according to claim 1.

18. A method of treating cancer selected from the group consisting of ovarian cancer, prostate cancer, breast cancer, skin cancer, melanoma, metastatic melanoma, colon cancer, lung cancer, pancreatic cancer, gastric cancer, bladder cancer, Ewing's sarcoma, osteosarcoma, glioblastoma, lymphoma, leukemia, multiple myeloma, head and neck cancer, brain cancer, kidney cancer, bone cancer, liver cancer, hepatocarcinoma and thyroid cancer in a subject comprising the step of administering to the subject a compound according to claim 1.

* * * * *

UNITED STATES PATENT AND TRADEMARK OFFICE
CERTIFICATE OF CORRECTION

PATENT NO. : 9,073,880 B2  
APPLICATION NO. : 13/976876  
DATED : July 7, 2015  
INVENTOR(S) : Reuveni et al.

It is certified that error appears in the above-identified patent and that said Letters Patent is hereby corrected as shown below:

In the Claims

Column 47:
Line 12 (claim 16, line 1), after "insulin-like growth factor", delete "I" and insert -- 1 --.
Line 20 (claim 17, line 3), after "and breast cancer", delete "cell" and insert -- cell, --.

Signed and Sealed this
Twenty-seventh Day of October, 2015

Michelle K. Lee
*Director of the United States Patent and Trademark Office*